US008586205B2

(12) United States Patent
Zheng et al.

(10) Patent No.: US 8,586,205 B2
(45) Date of Patent: *Nov. 19, 2013

(54) COMPOUNDS FOR ORGANIC LIGHT EMITTING DIODE EMISSIVE LAYERS

(75) Inventors: Shijun Zheng, San Diego, CA (US); David T. Sisk, San Diego, CA (US); Brett T. Harding, Carlsbad, CA (US); Jensen Cayas, Bonita, CA (US); Sheng Li, Vista, CA (US); Amane Mochizuki, San Diego, CA (US); Hyunsik Chae, San Diego, CA (US); Sazzadur Rahman Khan, San Diego, CA (US); Liping Ma, San Diego, CA (US); Rebecca Bottger, Escondido, CA (US)

(73) Assignee: Nitto Denko Corporation, Osaka (JP)

(*) Notice: Subject to any disclaimer, the term of this patent is extended or adjusted under 35 U.S.C. 154(b) by 270 days.

This patent is subject to a terminal disclaimer.

(21) Appl. No.: 12/883,018

(22) Filed: Sep. 15, 2010

(65) Prior Publication Data

US 2011/0062386 A1  Mar. 17, 2011

Related U.S. Application Data

(60) Provisional application No. 61/242,897, filed on Sep. 16, 2009.

(51) Int. Cl.
*H01L 51/54* (2006.01)

(52) U.S. Cl.
USPC ........... 428/690; 428/917; 313/504; 313/505; 313/506; 257/40; 257/E51.05; 257/E51.026; 257/E51.032; 548/152; 548/234; 548/304.4

(58) Field of Classification Search
USPC ................ 428/690, 917; 313/504, 505, 506; 257/40, E51.05, E51.026, E51.032; 548/152, 271, 304.4
See application file for complete search history.

(56) References Cited

U.S. PATENT DOCUMENTS

| 2005/0084711 A1 | 4/2005 | Sasaki et al. |
| 2008/0111478 A1 | 5/2008 | Lyu et al. |
| 2010/0060154 A1 | 3/2010 | Nomura et al. |
| 2010/0179469 A1 | 7/2010 | Hammond et al. |
| 2012/0016449 A1 | 1/2012 | Mochizuki et al. |

FOREIGN PATENT DOCUMENTS

| CN | 101 104 795 | 1/2008 |
| JP | 2008150365 | 7/2008 |
| WO | WO 03/080760 | 10/2003 |
| WO | WO 2005/022962 | 3/2005 |
| WO | WO 2005/090512 A1 | 9/2005 |
| WO | WO 2007/029696 | 3/2007 |

(Continued)

OTHER PUBLICATIONS

Adachi, C. , et al., J. Appl. Phys. 90, 5048, 2001.

(Continued)

*Primary Examiner* — Gregory Clark
(74) *Attorney, Agent, or Firm* — Knobbe Martens Olson & Bear, LLP

(57) ABSTRACT

Disclosed herein are compounds represented by a formula:

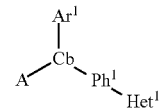

Wherein $Ar^1$, Cb, $Ph^1$, $Het^1$, and A are described herein. Compositions and light-emitting devices related thereto are also disclosed.

2 Claims, 6 Drawing Sheets

(56) References Cited

FOREIGN PATENT DOCUMENTS

| WO | WO 2010/021524 A2 | 2/2010 |
| WO | WO 2010/044607 | 4/2010 |
| WO | WO 2011/034967 | 3/2011 |

OTHER PUBLICATIONS

Baldo, M. A., et al., Nature, 403, 750, 2000.
Cai, X., et al., Appl. Phys. Lett. 92, 083308, 2008.
Chen, P., et al., Appl. Phys. Lett. 91, 023505, 2007.
D'Andrade, B. W., et al., Adv. Mater. 14, 1032, 2002.
D'Andrade, B. W., et al., Adv. Mater. 16, 1585, 2004.
D'Andrade, B. W., et al., Adv. Mater. 16, 624, 2004.
Ge, Z., et al., M. Chem. Mater. 2008, 20(7), 2532-2537.
Guan, M., et al., Org. Electronics, 7, 330-336, 2006.
Ho, Advanced Functional Materials (2008), 18(2), 319-331.
International Search Report and Written Opinion for PCT/US2010/048990, mailed Dec. 2, 2010.
Kido, J., et al., Chem. Mater. 2008, 20(5), 1691-1693.
Li, G. Cheng, F., et al., Appl. Phys. Lett. 82, 4224, 2003.
Lin, Synthetic Metals (2006), 156(9-10), 671-676.
Reineke, S., et al., Nature, 459, 234, 2009.
Schwartz, G., et al., Adv. Func. Mater., 2009, 19, 1-15.
Seo, J. H., et al., Appl. Phys. Lett. 90, 203507, 2007.
Sun, Y., et al., Nature, 440, 908, 2006.
Wong, Angewandte Chemie, International Edition (2006), 45(46), 7800-7803.
Wu, F. I., et al., J. Mater. Chem. 17, 167, 2007.
Ding, J., et al., Journal of Organometallic Chemistry, 2009, vol. 694, Issue 17, pp. 2700-2704.
Schwartz, G., et al., Appl. Phys. Lett., 2008, vol. 92, pp. 053311.
Schwartz, G., et al., Appl. Phys. Lett., 2008, vol. 93, pp. 073304.
Yang, X., et al., Journal of Physical Chemistry C, 2011, vol. 115, Issue 29, pp. 14347-14352.

COMPOUNDS FOR ORGANIC LIGHT EMITTING DIODE EMISSIVE LAYERS

CROSS-REFERENCE TO RELATED APPLICATIONS

This application claims the benefit of U.S. Provisional Application No. 61/242,897, filed Sep. 16, 2009, which is incorporated by reference herein in its entirety.

BACKGROUND OF THE INVENTION

1. Field of the Invention

The embodiments disclosed herein relate to compounds that may be useful in organic light emitting diode materials, such as ambipolar hosts for emissive materials of organic light emitting devices.

2. Description of the Related Art

White organic light emitting devices (WOLEDs) have attracted much attention and have been intensively studied due to their potential applications as backlight sources, full color displays, and for general lighting purposes. Among various device configurations to produce white light, devices with a single emissive layer have attracted much attention due to their simplicity of device fabrication and processing. Of the many types of single emissive layer that exist, devices employing phosphorescent materials in combination with proper host materials (all-phosphorescent), and the devices using a blue fluorescent host with a yellow phosphorescent emitter have attracted particular attention. These may be more effective than other types of devices for several reasons. For example, phosphorescent emitters can harvest both singlet and triplet excitons, and may thus have the potential of achieving 100% internal quantum efficiency. Another important consideration is that adding host materials not only may reduce concentration quenching of the emissive materials but may also reduce the overall cost of a device because the emissive materials may be more expensive than host materials. Additionally, fabrication of single layer devices may be much easier and may be more cost effective than multiple layer devices.

Therefore, development of effective host materials is important to improving the efficiency of WOLEDs. It may generally be desirable that a host transport both holes and electrons efficiently at same speed, and have a triplet energy high enough to effectively confine the triplet excitons on the guest molecules. Many host materials may be a mixture of hole-transport material and electron-transport material, which may pose potential problems such as phase separation, aggregation and lack of uniformity, and unequal material degradation. Development of single molecule ambipolar hosts (e.g. a host molecule which may transport both holes and electrons effectively) may provide improvement in these areas.

Synthesis and studies of some ambipolars host used in either single color or white organic light emitting diode (OLED) device applications have been reported. Many of them, however, may have either unbalanced hole-transport and electron-transport properties, or the devices made thereof may have showed only moderate efficiency.

SUMMARY OF THE INVENTION

Some embodiments provide a compound represented by a formula:

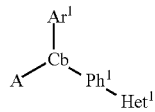

(Formula 1)

wherein Cb may be optionally substituted carbazole; A may be absent, or may be $Ph^2$ or $Ph^2$-$Het^2$; $Ph^1$ and $Ph^2$ may independently be optionally substituted phenyl; $Ar^1$ may be optionally substituted $C_{6-10}$ aryl; and $Het^1$ and $Het^2$ are independently optionally substituted benzimidazol-2-yl, optionally substituted benzothiazol-2-yl, or optionally substituted benzoxazol-2-yl.

Some embodiments provide a light-emitting device comprising: a light-emitting layer comprising a compound described herein.

These and other embodiments are described in greater detail below.

DETAILED DESCRIPTION OF THE PREFERRED EMBODIMENT

Figure 1:
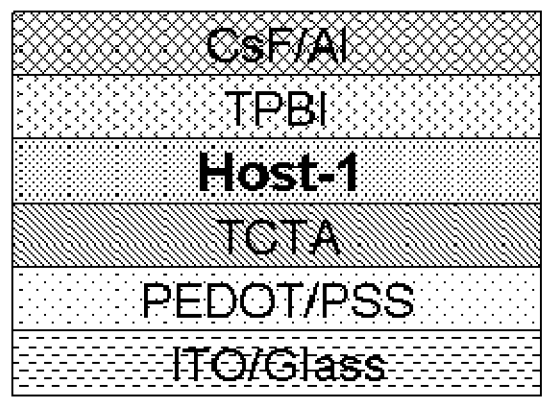
FIG. 1 is a schematic diagram of a device according to some embodiments.

Unless otherwise indicated, when a chemical structural feature such as alkyl or aryl is referred to as being "optionally substituted," it is meant that the feature may have no substituents (i.e. be unsubstituted) or may have one or more substituents. A feature that is "substituted" has one or more substituents. The term "substituent" has the ordinary meaning known to one of ordinary skill in the art. In some embodiments, the substituent may be an ordinary organic moiety known in the art, which may have a molecular weight (e.g. the sum of the atomic masses of the atoms of the substituent) of less than about 500 g/m, about 300 g/m, about 200 g/m, about 100 g/m, or about 50 g/m. In some embodiments, the substituent comprises: 0-30, 0-20, 0-10, or 0-5 carbon atoms; and 0-30, 0-20, 0-10, or 0-5 heteroatoms independently selected from: N, O, S, Si, F, Cl, Br, or I; provided that the substituent comprises at least one atom selected from: C, N, O, S, Si, F, Cl, Br, or I. Examples of substituents include, but are not limited to, alkyl, alkenyl, alkynyl, optionally substituted carbazolyl, optionally substituted aryl, optionally substituted diarylamino, optionally substituted heteroaryl, heteroalicyclyl, aralkyl, heteroaralkyl, (heteroalicyclyl)alkyl, hydroxy, protected hydroxy, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, halohydrocarbyl, haloalkyl, haloalkoxyl, trihalomethanesulfonyl, trihalomethanesulfonamido, and amino, including mono- and di-substituted amino groups, and the protected derivatives thereof.

In some embodiments, the substituents include, but are not limited to, $C_{1-6}$ alkyl, $C_{1-6}$ alkenyl, $C_{1-6}$ alkynyl, carbazolyl, $C_{6-10}$ aryl, $C_{12-20}$ diarylamino, $C_{2-10}$ heteroaryl, $C_{3-6}$ heteroalicyclyl, hydroxy, $C_{1-6}$ alkoxy, $C_{1-6}$ aryloxy, $C_{1-6}$ acyl, $C_{1-6}$ ester, mercapto, $C_{1-6}$ alkylthio, $C_{1-6}$ arylthio, cyano, halogen, carbonyl, thiocarbonyl, $C_{1-6}$ O-carbamyl, $C_{1-6}$ N-carbamyl, $C_{1-6}$ O-thiocarbamyl, $C_{1-6}$ N-thiocarbamyl, $C_{1-6}$ C-amido, $C_{1-6}$ N-amido, $C_{1-6}$ S-sulfonamido, $C_{1-6}$ N-sulfonamido, C-carboxy, protected C-carboxy, O-carboxy, isocyanato, thiocyanato, isothiocyanato, nitro, $C_{1-6}$ haloalkyl, $C_{1-6}$ haloalkoxyl, and $C_{1-6}$ amino, including mono- and di-substituted amino groups, and the protected derivatives thereof.

Substituents such as aryl, phenyl, or heteraryl, or substituents which include an aryl, a phenyl, or a heteroaryl portion, may themselves be further substituted to include any substituent indicated above, wherein any further substituent may be attached to the aryl ring, the phenyl ring, or the heteraryl ring portion of the parent substituent. In some embodiments, an aryl, a phenyl, or a heteroaryl present as a substituent or part of a substituent may be optionally substituted with one or more further substituents such as: alkyl, alkenyl, alkynyl, hydroxy, alkoxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, sulfonyl, halohydrocarbyl, haloalkyl, haloalkoxyl, trihalomethanesulfonyl, trihalomethanesulfonamido, and amino, including mono- and di-substituted amino groups, and the like.

As used herein, the term "carbazole" refers to the ring system:

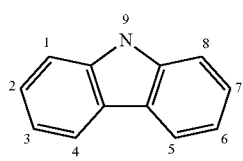

Various positions on the ring system where a substituent can attach to are indicated by the numbers on the ring system above. When optionally substituted, the addition of a substituent may occur at any possible position. The numbers may be used to refer to a position of a particular feature. For example, if A attaches at the 3-position, $Ph^1$ attaches at the 6-position, and $Ar^1$ attaches at the 9-position, a structure of Formula 2 may be obtained, wherein $R^a$, $R^b$, $R^c$, $R^d$, $R^e$, and $R^f$ may independently be H or a substituent, such as any substituent described herein. Attachment to the rest of the molecule may occur at any possible position.

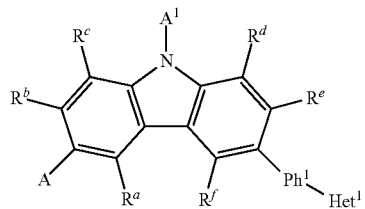

(Formula 2)

As used herein, the term "aryl" refers to an aromatic ring or ring system such as phenyl, naphthyl, etc. The structures depicted below represent some non-limiting examples of types of optionally substituted phenyl. The names of the structures are indicted below the structures:

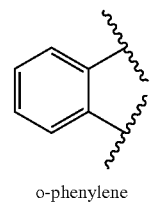

o-phenylene

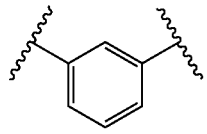

m-phenylene

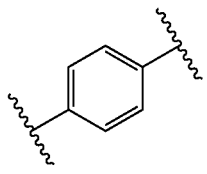

p-phenylene

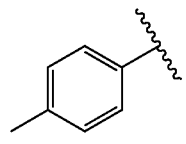

4-methylphenyl

When optionally substituted, the addition of a substituent may occur at any possible position.

The names for several other moieties used herein are indicated with the corresponding structures below:

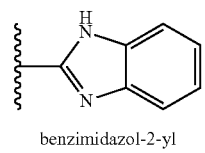

benzimidazol-2-yl

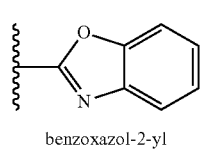

benzoxazol-2-yl

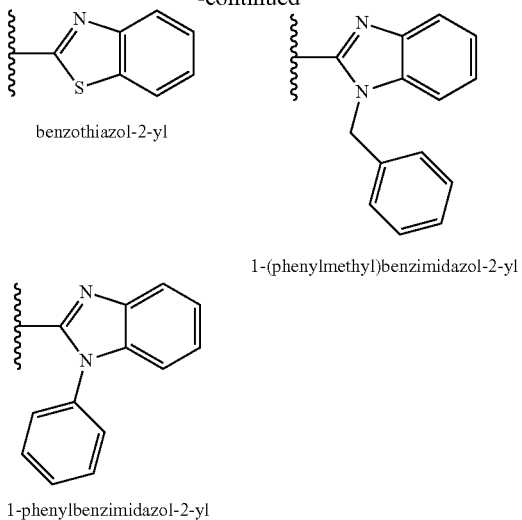

benzothiazol-2-yl 1-(phenylmethyl)benzimidazol-2-yl 1-phenylbenzimidazol-2-yl

When optionally substituted, the addition of a substituent may occur at any possible position.

As used herein, the term "1-((4-halophenyl)methyl)benzimidazol-2-yl" refers to the ring system:

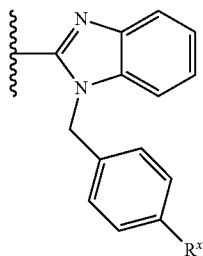

wherein $R^x$ may be a halogen such as F, Cl, Br, and I. When optionally substituted, the addition of a substituent may occur at any possible position.

An expression such as "$C_{1-10}$" (e.g. "$C_{1-10}$ alkyl") or "$C_{6-10}$" (e.g. "$C_{6-10}$ aryl") refers to the number of carbon atoms in a moiety, and similar expressions have similar meanings. If a moiety is optionally substituted, such as "optionally substituted $C_{6-10}$ aryl," the designation of the number of carbon atoms such as "$C_{6-10}$" refers to the parent moiety only (e.g. the ring carbons of aryl) and does not characterize or limit any substituent on the moiety.

As used herein, the term "hydrocarbyl" refers to a moiety composed of carbon and hydrogen. Hydrocarbyl includes alkyl, alkenyl, alkynyl, aryl, etc., and combinations thereof, and may be linear, branched, cyclic, or a combination thereof. Hydrocarbyl may be bonded to any other number of moieties (e.g. be bonded to 1 other group, such as —$CH_3$, —CH=$CH_2$, etc.; 2 other groups, such as -phenyl-, —C≡C— etc.; or any number of other groups) that the structure may bear, and in some embodiments, may contain from one to thirty-five carbon atoms. Examples of hydrocarbyl groups include but are not limited to $C_1$ alkyl, $C_2$ alkyl, $C_2$ alkenyl, $C_2$ alkynyl, $C_3$ alkyl, $C_3$ alkenyl, $C_3$ alkynyl, $C_4$ alkyl, $C_4$ alkenyl, $C_4$ alkynyl, $C_5$ alkyl, $C_5$ alkenyl, $C_5$ alkynyl, $C_6$ alkyl, $C_6$ alkenyl, $C_6$ alkynyl, phenyl, etc.

As used herein the term "alkyl" refers to a moiety composed of carbon and hydrogen containing no double or triple bonds. Alkyl may be linear alkyl, branched alkyl, cycloalkyl, or a combination thereof, and in some embodiments, may contain from one to thirty-five carbon atoms. In some embodiments, alkyl may include $C_{1-10}$ linear alkyl, such as methyl (—$CH_3$), ethyl (—$CH_2CH_3$), n-propyl (—$CH_2CH_2CH_3$), n-butyl (—$CH_2CH_2CH_2CH_3$), n-pentyl (—$CH_2CH_2CH_2CH_2CH_3$), n-hexyl (—$CH_2CH_2CH_2CH_2CH_2CH_3$), etc.; $C_{3-10}$ branched alkyl, such as $C_3H_7$ (e.g. iso-propyl), $C_4H_9$ (e.g. branched butyl isomers), $C_5H_{11}$ (e.g. branched pentyl isomers), $C_6H_{13}$ (e.g. branched hexyl isomers), $C_7H_{15}$ (e.g. heptyl isomers), etc.; $C_{3-10}$ cycloalkyl, such as $C_3H_6$ (e.g. cyclopropyl), $C_4H_8$ (e.g. cyclobutyl isomers such as cyclobutyl, methylcyclopropyl, etc.), $C_5H_{10}$ (e.g. cyclopentyl isomers such as cyclopentyl, methylcyclobutyl, dimethylcyclopropyl, etc.) $C_6H_{12}$ (e.g. cyclohexyl isomers), $C_7H_{15}$ (e.g. cycloheptyl isomers), etc.; and the like.

As used herein, the term "alkoxy" refers to —O-alkyl, such as —$OCH_3$, —$OC_2H_5$, —$OC_3H_7$ (e.g. propoxy isomers such as isopropoxy, n-propoxy, etc.), —$OC_4H_9$ (e.g. butyoxy isomers), —$OC_5H_{11}$ (e.g. pentoxy isomers), —$OC_6H_{13}$ (e.g. hexoxy isomers), —$OC_7H_{15}$ (e.g. heptoxy isomers), etc.

As used herein, the term "halo" refers to a halogen, such as F, Cl, Br, or I.

As used herein, the term "haloalkyl" refers to alkyl having one or more halo substituents. The term "fluoroalkyl" refers to alkyl having one or more fluoro substituents. The term "perfluoroalkyl" refers to fluoroalkyl wherein all hydrogen atom are replaced by fluoro such as —$CF_3$, —$C_2F_5$, —$C_3F_7$, —$C_4F_9$, etc.

As used herein, the term "acyl" refers to —$COR^0$, wherein $R^0$ may be optionally substituted hydrocarbyl. In some embodiments, acyl includes formyl, acetyl, propionoyl, butyryl, pentanoyl, hexanoyl, benzoyl, etc.

The term "work function" has the ordinary meaning known to one of ordinary skill in the art. In some embodiments, the "work function" of a metal refers to a measure of the minimum energy required to extract an electron from the surface of the metal.

The term "high work function metal" has the ordinary meaning known to one of ordinary skill in the art. In some embodiments, a "high work function metal" includes a metal or alloy that easily injects holes and typically has a work function greater than or equal to 4.5.

The term "low work function metal" has the ordinary meaning known to one of ordinary skill in the art. In some embodiments, a "low work function metal" includes a metal or alloy that easily loses electrons and typically has a work function less than 4.3.

The expression "white light-emitting" has the ordinary meaning known to one of ordinary skill in the art. In some embodiments, a material is white light-emitting if it emits white light. In some embodiments, white light is light having the approximate CIE color coordinates (X=⅓, Y=⅓). The CIE color coordinates (X=⅓, Y=⅓) may be defined as the achromatic point. The X and Y color coordinates may be weights applied to the CIE primaries to match a color. A more detailed description of these terms may be found in CIE 1971, International Commission on Illumination, Colorimetry: Official Recommendations of the International Commission on Illumination, Publication CIE No. 15 (E-1.3.1) 1971, Bureau Central de la CIE, Paris, 1971 and in F. W. Billmeyer, Jr., M. Saltzman, Principles of Color Technology, 2nd edition, John Wiley & Sons, Inc., New York, 1981, both of which are hereby incorporated by reference in their entireties. The color rendering index (CRI) refers to the ability to render various colors and has values ranging from 0 to 100, with 100 being the best.

The term "deep blue emitting" has the ordinary meaning known to one of ordinary skill in the art. In some embodiments, a material is "deep blue emitting" if it emits deep blue light. In some embodiments, deep blue light is light having the approximate CIE color coordinates (X=[0.14], Y=[0.08], CIE 1931).

Some embodiments provide a compound represented by Formula 1:

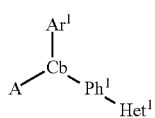

(Formula 1)

wherein Cb may be optionally substituted carbazole. In some embodiments, A may attach to Cb at the 3-position, and may be absent or may be $Ph^2$ or $Ph^2$-$Het^2$. In embodiments where A may be $Ph^2$ or $Ph^2$-$Het^2$, $Ph^2$ may attach directly to Cb at the 3-position. $Ph^1$ may attach to Cb at the 6-position, and $Ar^1$ may attach to Cb at the 9-position. In some embodiments, the optionally substituted carbazole may have 0, 1, 2, 3, or 4 substituents independently selected from the group consisting of $C_{1-10}$ alkyl (such as $C_{1-10}$ linear alkyl, $C_{3-10}$ branched alkyl, or $C_{3-10}$ cycloalkyl), $C_{1-10}$ alkoxy, and halo.

With respect to Formula 1, A may be absent, or may be $Ph^2$ or $Ph^2$-$Het^2$. Thus, some embodiments relate to compounds represented by Formula 3, Formula 4, or Formula 5.

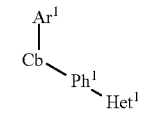

(Formula 3)

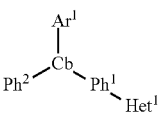

(Formula 4)

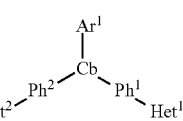

(Formula 5)

With respect to any relevant formula above, Cb may be optionally substituted carbazole. The optionally substituted carbazole may have 0, 1, 2, 3, or 4 substituents. In some embodiments, the substituents of Cb are not thiol, an ester, or an amide. In some embodiments, the substituents of Cb are independently selected from the group consisting of $C_{1-10}$ alkyl; hydroxyl; $C_{1-10}$ alkoxy; —$NR^1R^2$, wherein $R^1$ and $R^2$ are independently H or $C_{1-10}$ alkyl; halo; $C_{1-10}$ haloalkyl; $C_{1-10}$ perfluoroalkyl; $C_{1-10}$ acyl; $CO_2H$; cyano; cyanate; isocyanate; nitro; etc. In some embodiments, Cb has 0, 1, 2, 3, or 4 substituents independently selected from the group consisting of: $C_{1-10}$ alkyl, $C_{1-10}$ alkoxy, F, Cl, Br, and I. In some embodiments, Cb has 0, 1, 2, 3, or 4 substituents independently selected from the group consisting of: $C_{1-3}$ alkyl, F and Cl. In some embodiments, Cb may be unsubstituted carbazole.

With respect to any relevant formula above, $Ar^1$ may be optionally substituted $C_{6-10}$ aryl. In some embodiments, $Ar^1$ may be phenyl or methylphenyl, each substituted with 0, 1, 2, 3, 4, or 5 substituents independently selected from: $C_{1-10}$ alkyl; hydroxyl; $C_{1-10}$ alkoxy; —$(OR^3)_pOR^4$ wherein $R^3$ may be —$CH_2CH_2$—, —$CH_2CH(CH_3)$—, or —$CH(CH_3)CH_2$—, $R^4$ may be H or $C_{1-3}$ alkyl, and p may be 1, 2, 3, or 4; halo; $C_{1-10}$ haloalkyl; $C_{1-10}$ perfluoroalkyl; $C_{1-10}$ acyl; —$CO_2R^1$, —$OC(O)R^1$, —$NR^1R^2$, —$C(O)NR^1R^2$, —$NR^1C(O)R^2$, —$OC(O)NR^1R^2$, or —$NR^1CO_2R^2$, wherein $R^1$ and $R^2$ are independently H or $C_{1-10}$ alkyl; cyano; cyanate; isocyanate; nitro; etc. In some embodiments, $Ar^1$ may be methylphenyl, such as 2-, 3-, or 4-methylphenyl, each optionally substituted with 1, 2, 3, or 4 substituents independently selected from $C_{1-3}$ alkyl, F and Cl. In some embodiments, $Ar^1$ may be unsubstituted phenyl, phenyl, or 4-methylphenyl.

With respect to any relevant formula above, $Ph^1$ may be optionally substituted phenyl. In some embodiments, $Ph^1$ may be phenyl, such as o-phenylene, m-phenylene, or p-phenylene, substituted with 0, 1, 2, 3, or 4 substituents independently selected from: $C_{1-10}$ alkyl; hydroxyl; $C_{1-10}$ alkoxy; —$(OR^3)_pOR^4$ wherein $R^3$ may be —$CH_2CH_2$—, —$CH_2CH(CH_3)$—, or —$CH(CH_3)CH_2$—, $R^4$ may be H or $C_{1-3}$ alkyl, and p may be 1, 2, 3, or 4; halo; $C_{1-10}$ haloalkyl; $C_{1-10}$ perfluoroalkyl; $C_{1-10}$ acyl; —$CO_2R^1$, —$OC(O)R^1$; —$NR^1R^2$, —$C(O)NR^1R^2$; —$NR^1C(O)R^2$; —$OC(O)NR^1R^2$; or —$NR^1CO_2R^2$, wherein $R^1$ and $R^2$ are independently H or $C_{1-10}$ alkyl; cyano; cyanate; isocyanate; nitro; etc. In some embodiments, $Ph^1$ may be phenyl, such as o-phenylene, m-phenylene, or p-phenylene, which has 0, 1, 2, 3, or 4 substituents independently selected from: $C_{1-10}$ alkyl; hydroxyl; halo; perfluoroalkyl; $C_{1-10}$ acyl; $C_{1-10}$ amides attaching at the carbonyl; $C_{1-10}$ esters attaching at the carbonyl; $CO_2H$; cyano; cyanate; isocyanate; nitro; etc. In some embodiments, $Ph^1$ may be phenyl, such as o-phenylene, m-phenylene, or p-phenylene, each optionally substituted with 1, 2, 3, or 4 substituents independently selected from the group consisting of: $C_{1-3}$ alkyl, F and Cl. In some embodiments, $Ph^1$ may be unsubstituted o-phenylene, unsubstituted m-phenylene, or unsubstituted p-phenylene With respect to any relevant formula above, $Het^1$ may be optionally substituted benzimidazol-2-yl, optionally substituted benzothiazol-2-yl, or optionally substituted benzoxazol-2-yl. In some embodiments, $Het^1$ may be selected from the group consisting of optionally substituted 1-phenylbenzimidazol-2-yl, optionally substituted 1-(phenylmethyl)benzimidazol-2-yl, and optionally substituted 1-((4-halophenyl)methyl)benzimidazol-2-yl. In some embodiments, Het $^1$has 0, 1, 2, 3, 4, or 5 substituents independently selected from: optionally substituted $C_{6-30}$ aryl; $C_{1-10}$ alkyl; hydroxyl; $C_{1-10}$ alkoxy; —$(OR^3)_pOR^4$ wherein $R^3$ may be —$CH_2CH_2$—, —$CH_2CH(CH_3)$—, or —$CH(CH_3)CH_2$—, $R^4$ may be H or $C_{1-3}$ alkyl, and p may be 1, 2, 3, or 4; halo; $C_{1-10}$ haloalkyl; $C_{1-10}$ perfluoroalkyl; $C_{1-10}$ acyl; —$CO_2R^1$, —$OC(O)R^1$, —$NR^1R^2$, —$C(O)NR^1R^2$, —$NR^1C(O)R^2$, —$OC(O)NR^1R^2$, or —$NR^1CO_2R^2$, wherein $R^1$ and $R^2$ are independently H or $C_{1-10}$ alkyl; cyano; cyanate; isocyanate; nitro, etc.

In some embodiments, $Het^1$ may be unsubstituted 1-phenylbenzimidazol-2-yl, unsubstituted 1-(phenylmethyl)benzimidazol-2-yl, and unsubstituted 1-((4-halophenyl)methyl)benzimidazol-2-yl.

In some embodiments, the substituents of $Het^1$ may include halo; $C_{1-10}$ perfluoroalkyl; $C_{1-10}$ acyl; optionally substituted $C_{6-30}$ aryl; $C_{1-10}$ alkyl; $C_{1-10}$ alkoxy; —$C(O)NR^1R^2$; —$CO_2R^1$; cyano; cyanate; isocyanate; nitro; etc. In some embodiments, $Het^1$ may be selected from the group consisting of 1-phenylbenzimidazol-2-yl, 1-(phenylmethyl)benzimidazol-2-yl, and 1-(4-halophenyl)methylbenzimidazol-2-yl, and $Het^1$ may be optionally substituted with 1, 2, 3, or 4 substituents independently selected from the group consisting of: optionally substituted $C_{6-30}$ aryl, $C_{1-10}$ alkyl, and $C_{1-10}$ alkoxy. In some embodiments, $Het^1$ may be benzoxazol-2-yl optionally substituted with 1, 2, 3, or 4 substituents independently selected from the group consisting of: optionally substituted $C_{6-30}$ aryl, $C_{1-10}$ alkyl, and $C_{1-10}$ alkoxy. In some embodiments, $Het^1$ may be benzothiazol-2-yl optionally substituted with 1, 2, 3, or 4 substituents independently selected from the group consisting of: optionally substituted $C_{6-30}$ aryl, $C_{1-10}$ alkyl, and $C_{1-10}$ alkoxy.

With respect to any relevant formula above, $Ph^2$ may be optionally substituted phenyl. In some embodiments, $Ph^2$ may be phenyl, such as o-phenylene, m-phenylene, or p-phenylene, which may be optionally substituted with 1, 2, 3, or 4, substituents independently selected from: $C_{1-10}$ alkyl; hydroxyl; $C_{1-10}$ alkoxy; —$(OR^3)_pOR^4$ wherein $R^3$ may be —$CH_2CH_2$—, —$CH_2CH(CH_3)$—, or —$CH(CH_3)CH_2$—, $R^4$ may be H or $C_{1-3}$ alkyl, and p may be 1, 2, 3, or 4; halo; $C_{1-10}$ haloalkyl; $C_{1-10}$ perfluoroalkyl; $C_{1-10}$ acyl; —$CO_2R^1$, —$OC(O)R^1$, —$NR^1R^2$, —$CONR^1R^2$, —$NR^1COR^2$, —$OCONR^1R^2$, or —$NR^1CO_2R^2$, wherein $R^1$ and $R^2$ are independently H or $C_{1-10}$ alkyl; cyano; cyanate; isocyanate; nitro; etc. In some embodiments, $Ph^2$ may be phenyl, such as o-phenylene, m-phenylene, or p-phenylene, which is optionally substituted with 1, 2, 3, or 4 substituents independently selected from: $C_{1-10}$ alkyl; hydroxyl; halo; perfluoroalkyl; $C_{1-10}$ acyl; $C_{1-10}$ amides attaching at the carbonyl; $C_{1-10}$ esters attaching at the carbonyl; $CO_2H$; cyano; cyanate; isocyanate; nitro; etc. In some embodiments, $Ph^2$ may be unsubstituted. In some embodiments, $Ph^2$ may be phenyl, such as o-phenylene, m-phenylene, or p-phenylene, each optionally substituted with 1, 2, 3, or 4 substituents independently selected from the group consisting of: $C_{1-3}$ alkyl, F and Cl. In some embodiments, $Ph^2$ may be unsubstituted phenyl, unsubstituted o-phenylene, unsubstituted m-phenylene, or unsubstituted p-phenylene With respect to any relevant formula above, $Het^2$ may be optionally substituted benzimidazol-2-yl, optionally substituted benzothiazol-2-yl, or optionally substituted benzoxazol-2-yl. In some embodiments, $Het^2$ may be selected from the group consisting of optionally substituted 1-phenylbenzimidazol-2-yl, optionally substituted 1-(phenylmethyl)benzimidazol-2-yl, and optionally substituted 1-((4-halophenyl) methyl)benzimidazol-2-yl. In some embodiments, $Het^2$ may have 0, 1, 2, 3, 4, or 5 substituents independently selected from: optionally substituted $C_{6-30}$ aryl; $C_{1-10}$ alkyl; hydroxyl; $C_{1-10}$ alkoxy; —$(OR^3)_pOR^4$ wherein $R^3$ may be —$CH_2CH_2$—, —$CH_2CH(CH_3)$—, or —$CH(CH_3)CH_2$—, $R^4$ may be H or $C_{1-3}$ alkyl, and p may be 1, 2, 3, or 4; halo; $C_{1-10}$ haloalkyl; $C_{1-10}$ perfluoroalkyl; $C_{1-10}$ acyl; —$CO_2R^1$, —$OC(O)R^1$, —$NR^1R^2$, —$CONR^1R^2$, —$NR^1COR^2$, —$OCONR^1R^2$, or —$NR^1CO_2R^2$, wherein $R^1$ and $R^2$ are independently H or $C_{1-10}$ alkyl; cyano; cyanate; isocyanate; nitro; etc. In some embodiments, the substituents of $Het^2$ may include halo; optionally substituted $C_{6-30}$ aryl; $C_{1-10}$ alkyl; $C_{1-10}$ alkoxy; perfluoroalkyl; $C_{1-10}$ acyl; $C_{0-10}$ amines such as $NR^1R^2$, wherein $R^1$ and $R^2$ are independently H or alkyl, such as $NH_2$, $NHCH_3$, $N(CH_3)_2$, etc.; $C_{1-10}$ amides attaching at the carbonyl; $C_{1-10}$ esters attaching at the carbonyl; —$CO_2CH_2$, etc.; $CO_2H$; cyano; cyanate; isocyanate; nitro; etc. In some embodiments, $Het^2$ may be selected from the group consisting of 1-phenylbenzimidazol-2-yl, 1-(phenylmethyl)benzimidazol-2-yl, and 1-((4-halophenyl)methyl)benzimidazol-2-yl, and $Het^2$ has 0, 1, 2, 3, or 4 substituents independently selected from the group consisting of: optionally substituted $C_{6-30}$ aryl, $C_{1-10}$ alkyl, or $C_{1-10}$ alkoxy. In some embodiments, $Het^2$ may be unsubstituted 1-phenylbenzimidazol-2-yl, unsubstituted 1-(phenylmethyl)benzimidazol-2-yl, and unsubstituted 1-((4-halophenyl)methyl)benzimidazol-2-yl. In some embodiments, $Het^2$ may be benzothiazol-2-yl optionally substituted with 1, 2, 3, or 4 substituents independently selected from the group consisting of: optionally substituted $C_{6-30}$ aryl, $C_{1-10}$ alkyl, and $C_{1-10}$ alkoxy. In some embodiments, $Het^2$ may be benzoxazol-2-yl optionally substituted with 1, 2, 3, or 4 substituents independently selected from the group consisting of: optionally substituted $C_{6-30}$ aryl, $C_{1-10}$ alkyl, and $C_{1-10}$ alkoxy.

With respect to Formula 2, in some embodiments, $R^a$, $R^b$, $R^c$, $R^d$, $R^e$, and $R^f$ may be independently selected from the group consisting of H, $C_{1-10}$ alkyl; hydroxyl; $C_{1-10}$ alkoxy; —$NR^1R^2$, wherein $R^1$ and $R^2$ are independently H or $C_{1-10}$ alkyl; halo; $C_{1-10}$ haloalkyl; $C_{1-10}$ perfluoroalkyl; $C_{1-10}$ acyl; $CO_2H$; cyano; cyanate; isocyanate; nitro; etc. In some embodiments, $R^a$, $R^b$, $R^c$, $R^d$, $R^e$, and $R^f$ may be independently selected from the group consisting of: H, $C_{1-10}$ alkyl, $C_{1-10}$ alkoxy, F, Cl, Br, and I. $R^a$, $R^b$, $R^c$, $R^d$, $R^e$, and $R^f$ may be independently selected from the group consisting of: H, $C_{1-3}$ alkyl, F and Cl.

With respect to Formula 3, in some embodiments, $Ar^1$ may be optionally substituted phenyl, $Ph^1$ may be optionally substituted o-phenylene, and $Het^1$ may be optionally substituted 1-phenylbenzimidazol-2-yl. In some embodiments, the substituents of $Ar^1$, Cb, $Ph^1$, and $Het^1$ may be independently selected from: $C_{1-6}$ alkyl; hydroxyl; $C_{1-6}$ alkoxy; halo; $C_{1-6}$ perfluoroalkyl; $C_{1-6}$ acyl; —$CO_2R^5$, —$OC(O)R^5$, —$NR^5R^6$, —$C(O)NR^5R^6$, —$NR^5C(O)R^6$, —$OC(O)NR^5R^6$, or —$NR^5CO_2R^6$, wherein $R^5$ and $R^6$ are independently H or $C_{1-5}$ alkyl; cyano; cyanate; isocyanate; and nitro. In some embodiments, the substituents of $Ar^1$, Cb, $Ph^1$, and $Het^1$ may be independently selected from: $C_{1-3}$ alkyl, hydroxyl, $C_{1-3}$ alkoxy, F, Cl, Br, I, and $C_{1-3}$ perfluoroalkyl.

With respect to Formula 4, in some embodiments, $Ar^1$ may be optionally substituted phenyl, $Ph^1$ may be optionally substituted m-phenylene, and $Het^1$ may be optionally substituted 1-phenylbenzimidazol-2-yl. In some embodiments, $Ar^1$ may be optionally substituted phenyl, $Ph^1$ may be optionally substituted p-phenylene, and $Het^1$ may be optionally substituted 1-phenylbenzimidazol-2-yl. In some embodiments, $Ar^1$ may be optionally substituted phenyl, $Ph^1$ may be optionally substituted m-phenylene, and $Het^1$ may be optionally substituted benzoxazol-2-yl. In some embodiments, $Ar^1$ may be optionally substituted phenyl, $Ph^1$ may be optionally substituted o-phenylene, and $Het^1$ may be optionally substituted benzoxazol-2-yl. In some embodiments, $Ar^1$ may be optionally substituted phenyl, $Ph^1$ may be optionally substituted p-phenylene, and $Het^1$ may be optionally substituted benzoxazol-2-yl. In some embodiments, the substituents of $Ar^1$, Cb, $Ph^1$, $Ph^2$, and $Het^1$ may be independently selected from: $C_{1-6}$ alkyl; hydroxyl; $C_{1-6}$ alkoxy; halo; $C_{1-6}$ perfluoroalkyl; $C_{1-6}$ acyl; —$CO_2R^5$, —$OC(O)R^5$, —$NR^5R^6$, —$C(O)NR^5R^6$, —$NR^5C(O)R^6$, —$OC(O)NR^5R^6$, or —$NR^5CO_2R^6$, wherein $R^5$ and $R^6$ are independently H or $C_{1-5}$ alkyl; cyano; cyanate; isocyanate; and nitro. In some embodiments, the substituents of $Ar^1$, Cb, $Ph^1$, $Ph^2$, and $Het^1$ may be independently selected from: $C_{1-3}$ alkyl, hydroxyl, $C_{1-3}$ alkoxy, F, Cl, Br, I, and $C_{1-3}$ perfluoroalkyl.

With respect to Formula 5, in some embodiments $Ar^1$ may be optionally substituted phenyl, $Ph^1$ and $Ph^2$ are independently optionally substituted p-phenylene, and $Het^1$ and $Het^2$ are independently optionally substituted 1-phenylbenzimidazol-2-yl. In some embodiments $Ar^1$ may be optionally substituted phenyl, $Ph^1$ and $Ph^2$ are independently optionally substituted m-phenylene, and $Het^1$ and $Het^2$ are independently optionally substituted 1-phenylbenzimidazol-2-yl. In some embodiments Ar¹ may be optionally substituted phenyl, Ph¹ and Ph² may be independently optionally substituted o-phenylene, and Het¹ and Het² may independently be optionally substituted 1-phenylbenzimidazol-2-yl. In some embodiments Ar¹ may be optionally substituted phenyl, Ph¹ and Ph² are independently optionally substituted p-phenylene, and Het¹ and Het² are independently optionally substituted benzoxazol-2-yl. In some embodiments Ar¹ may be optionally substituted phenyl, Ph¹ and Ph² are independently optionally substituted m-phenylene, and Het¹ and Het² are independently optionally substituted benzoxazol-2-yl. In some embodiments Ar¹ may be optionally substituted phenyl, Ph¹ and Ph² are independently optionally substituted o-phenylene, and Het¹ and Het² are independently optionally substituted benzoxazol-2-yl. In some embodiments, the substituents of Ar¹, Cb, Ph¹, Ph², Het¹, and Het² may be independently selected from: $C_{1-6}$ alkyl; hydroxyl; $C_{1-6}$ alkoxy; halo; $C_{1-6}$ perfluoroalkyl; $C_{1-6}$ acyl; —$CO_2R^5$, —$OC(O)R^5$, —$NR^5R^6$, —$C(O)NR^5R^6$, —$NR^5C(O)R^6$, —$OC(O)NR^5R^6$, or —$NR^5CO_2R^6$, wherein $R^5$ and $R^6$ are independently H or $C_{1-5}$ alkyl; cyano; cyanate; isocyanate; and nitro. In some embodiments, the substituents of Ar¹, Cb, Ph¹, Ph², Het¹, and Het² may be independently selected from: $C_{1-3}$ alkyl, hydroxyl, $C_{1-3}$ alkoxy, F, Cl, Br, I, and $C_{1-3}$ perfluoroalkyl.

In some embodiments related to Formula 1 or Formula 2, A is the same as Ph¹-Het¹. Similarly, with respect to Formula 5, in some embodiments Ph¹-Het¹ is the same as Ph²-Het².

Some embodiments relate to compounds selected from:

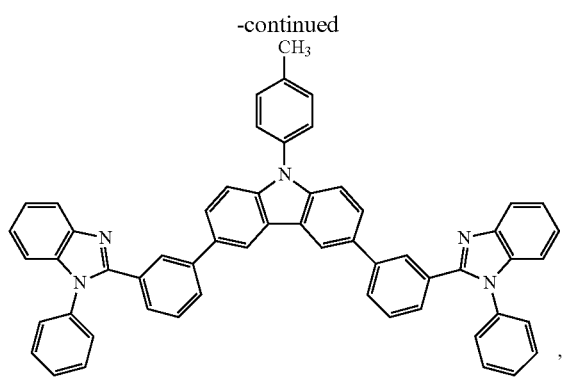

,

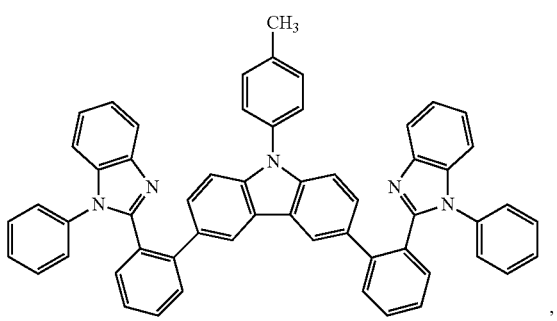

,

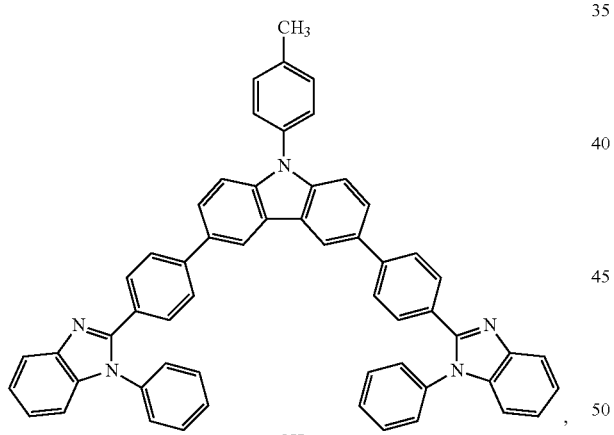

,

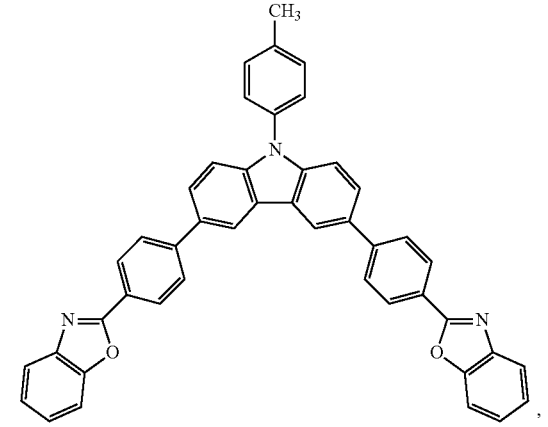

,

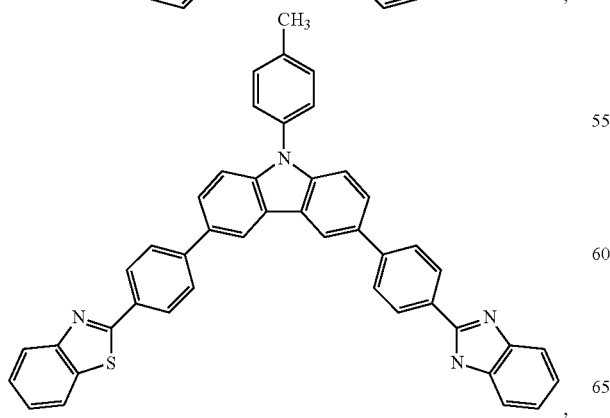

,

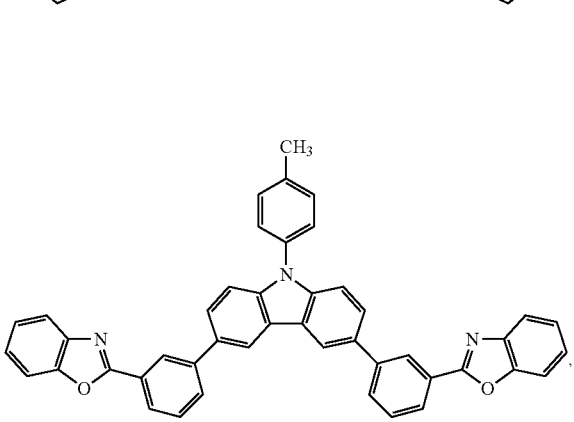

,

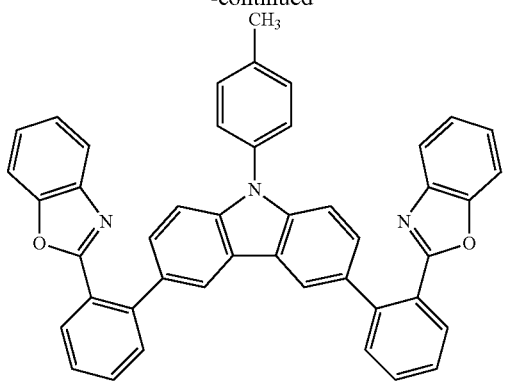
,
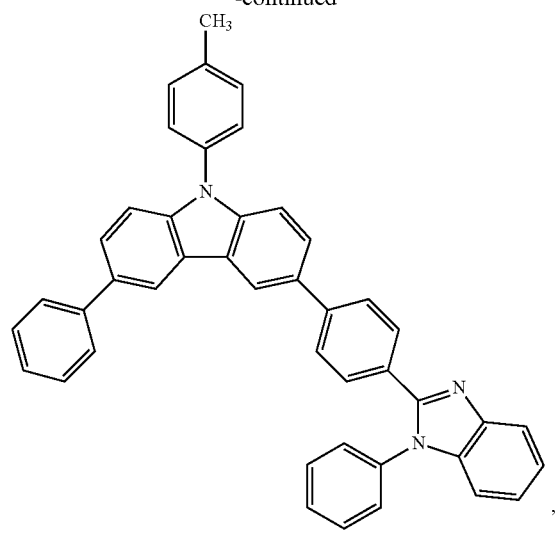
,
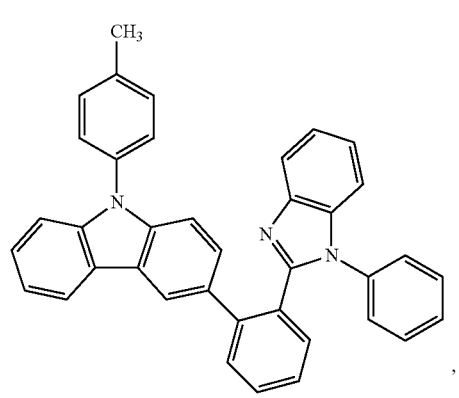
,
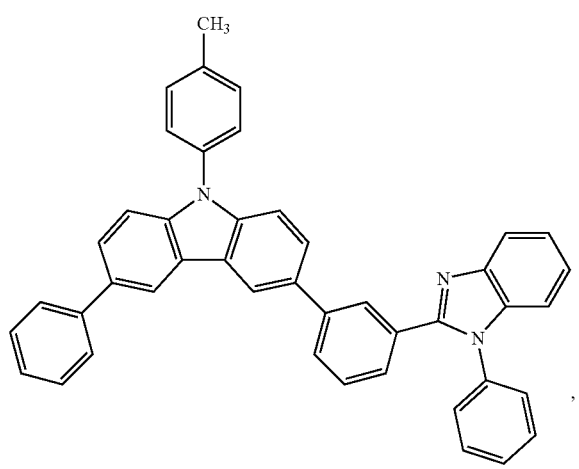
,
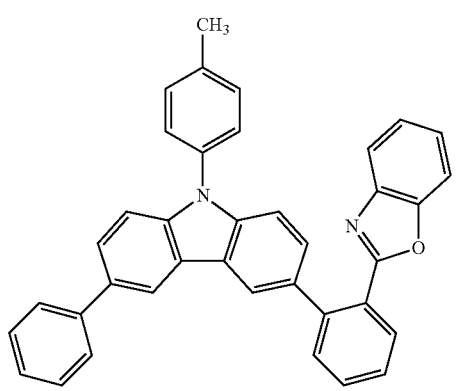
, and

-continued

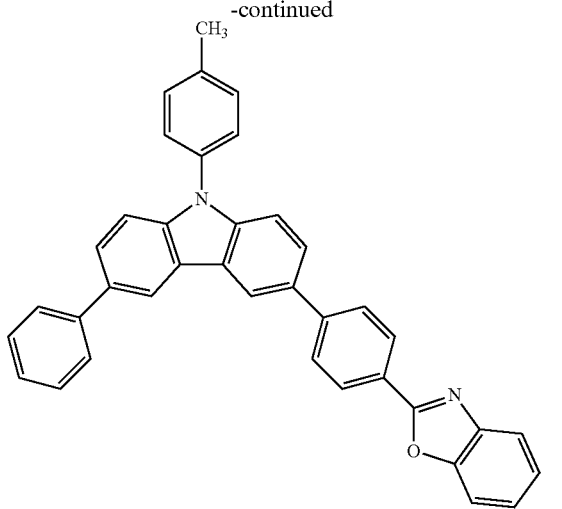

In some embodiments, the compounds described may be used as an emissive compound, as an ambipolar host in an organic light emitting diode emissive layer, or both. In some embodiments, the compounds disclosed herein may provide well balanced hole-transport and electron-transport mobility, which may lead to a simpler device structure with high quantum efficiency and low turn-on voltage. For example in some embodiments, the organic light emitting diode or device incorporating the presently described compounds may not have a hole transporting layer or an emissive layer. In some embodiments, these compounds may have high electrochemical stability, high thermal stability, a high glass transition temperature (Tg), and high photostability. Thus, these compounds may provide an OLED device with a longer lifetime than existing OLED devices.

The compounds and compositions described herein can be incorporated into light-emitting devices in various ways. For example, an embodiment provides a light-emitting device comprising: an anode layer comprising a high work function metal; a cathode layer comprising a low work function metal; and a light-emitting layer positioned between the anode layer and the cathode layer. The light-emitting device may be configured so that the anode can transfer holes to the light-emitting layer and the cathode can transfer electrons to the light-emitting layer. The light-emitting layer comprises the compounds and/or compositions disclosed herein.

An anode layer may comprise a conventional material such as a metal, mixed metal, alloy, metal oxide or mixed-metal oxide, or a conductive polymer. Examples of suitable metals include the metals in Groups 10, Group 11, and Group 12 transition metals. If the anode layer is to be light-transmitting, mixed-metal oxides of Groups 12, Group 13, and Group 14 metals or alloys thereof, such as zinc oxide, tin oxide, indium zinc oxide (IZO) or indium-tin-oxide (ITO) may be used. The anode layer may include an organic material such as polyaniline, e.g., as described in "Flexible light-emitting diodes made from soluble conducting polymer," Nature, vol. 357, pp. 477-479 (11 Jun. 1992). Examples of suitable high work function metals include but are not limited to Au, Pt, indium-tin-oxide (ITO), or alloys thereof. In some embodiments, the anode layer can have a thickness in the range of about 1 nm to about 1000 nm.

A cathode layer may include a material having a lower work function than the anode layer. Examples of suitable materials for the cathode layer include those selected from alkali metals of Group 1, Group 2 metals, Group 11, Group 12, and Group 13 metals including rare earth elements, lanthanides and actinides, materials such as aluminum, indium, calcium, barium, samarium and magnesium, and combinations thereof. Li-containing organometallic compounds, LiF, and $Li_2O$ may also be deposited between the organic layer and the cathode layer to lower the operating voltage. Suitable low work function metals include but are not limited to Al, Ag, Mg, Ca, Cu, Mg/Ag, LiF/Al, CsF, CsF/Al or alloys thereof. In some embodiments, the cathode layer can have a thickness in the range of about 1 nm to about 1000 nm.

The amount of the compounds disclosed herein in the light-emitting composition can vary. In one embodiment, the amount of a compound disclosed herein in the light-emitting layer may be in the range of from about 1% to about 100% by weight of the light-emitting layer. In another embodiment, the amount of a compound disclosed herein in the light-emitting layer may be in the range of from about 90% to about 99% by weight of the light-emitting layer. In another embodiment, the amount of a compound disclosed herein in the light-emitting layer may be about 97% by weight of the light-emitting layer. In some embodiments, the mass of the electroluminescent compound may be about 0.1% to about 10%, about 1% to about 5%, or about 3% of the mass of the emissive layer.

The thickness of the light-emitting layer may vary. In one embodiment, the light-emitting layer has a thickness in the range of from about 5 nm to about 200 nm. In another embodiment, the light-emitting layer has a thickness in the range of about 10 nm to about 150 nm.

In another embodiment, the light-emitting layer may also be configured to emit white light.

The compounds and compositions described herein may be useful in an emissive layer without requiring any additional hole-transport or electron-transport materials. Thus, in some embodiments, the light-emitting layer consists essentially of an electroluminescent compound and a compound disclosed herein. In some embodiments, the light-emitting layer consists essentially of a compound disclosed herein. In some embodiments, the light-emitting layer may comprise at least one hole-transport material or electron transport material in addition to a compound disclosed herein.

In some embodiments, a hole-transport material may comprise at least one of an aromatic-substituted amine, a carbazole, a polyvinylcarbazole (PVK), e.g. poly(9-vinylcarbazole); N,N'-bis(3-methylphenyl)N,N'-diphenyl-[1,1'-biphenyl]-4,4'-diamine (TPD); polyfluorene; a polyfluorene copolymer; poly(9,9-di-n-octylfluorene-alt-benzothiadiazole); poly(paraphenylene); poly[2-(5-cyano-5-methylhexyloxy)-1,4-phenylene]; 1,1-Bis(4-bis(4-methylphenyl)aminophenyl)cyclohexane; 2,9-Dimethyl-4,7-diphenyl-1,10-phenanthroline; 3,5-Bis(4-tert-butyl-phenyl)-4-phenyl[1,2,4]triazole; 3,4,5-Triphenyl-1,2,3-triazole; 4,4',4"-Tris(N-(naphthylen-2-yl)-N-phenylamino)triphenylamine; 4,4',4'-tris(3-methylphenylphenylamino)triphenylamine (MTDATA); 4,4'-bis[N-(naphthyl)-N-phenyl-amino]biphenyl (NPB); 4,4'-bis[N,N'-(3-tolyl)amino]-3,3'-dimethylbiphenyl (HMTPD); 4,4'-N,N'-dicarbazole-biphenyl (CBP); 1,3-N,N-dicarbazole-benzene (mCP); poly(9-vinylcarbazole) (PVK); a benzidine; a phenylenediamine; a phthalocyanine metal complex; a polyacetylene; a polythiophene; a triphenylamine; an oxadiazole; copper phthalocyanine; N,N'N"-1,3,5-tricarbazoloylbenzene (tCP); N,N'-bis(4-butylphenyl)-N,N'-bis(phenyl)benzidine; and the like.

In some embodiments, an electron-transport material may comprise at least one of 2-(4-biphenylyl)-5-(4-tert-butylphenyl)-1,3,4-oxadiazole (PBD); 1,3-bis(N,N-t-butyl-phenyl)-1,3,4-oxadiazole (OXD-7), 1,3-bis[2-(2,2'-bipyridine-6-yl)-1, 3,4-oxadiazo-5-yl]benzene; 3-phenyl-4-(1'-naphthyl)-5-phenyl-1,2,4-triazole (TAZ); 2,9-dimethyl-4,7-diphenyl-phenanthroline (bathocuproine or BCP); aluminum tris(8-hydroxyquinolate) (Alq3); and 1,3,5-tris(2-N-phenylbenzimidazolyl)benzene; 1,3-bis[2-(2,2'-bipyridine-6-yl)-1,3,4-oxadiazo-5-yl]benzene (BPY-OXD); 3-phenyl-4-(1'-naphthyl)-5-phenyl-1,2,4-triazole (TAZ), 2,9-dimethyl-4,7-diphenyl-phenanthroline (bathocuproine or BCP); and 1,3,5-tris[2-N-phenylbenzimidazol-z-yl]benzene (TPBI). In one embodiment, the electron transport layer may be aluminum quinolate ($Alq_3$), 2-(4-biphenylyl)-5-(4-tent-butylphenyl)-1,3,4-oxadiazole (PBD), phenanthroline, quinoxaline, 1,3,5-tris[N-phenylbenzimidazol-z-yl]benzene (TPBI), or a derivative or a combination thereof.

In some embodiments, the device comprises no electron transport or hole transport layer. In some embodiments, the device consists essentially of the anode layer, the cathode layer, and the light-emitting layer. In other embodiments, the light-emitting device may further comprise a hole-transport layer disposed between the anode and the light-emitting layer. The hole-transport layer may comprise at least one hole-transport material. Suitable hole-transport materials may include those listed above in addition to any others known to those skilled in the art.

In some embodiments, the light-emitting device may further comprise an electron-transport layer disposed between the cathode and the light-emitting layer. The electron-transport layer may comprise at least one electron-transport material. Suitable electron transport materials include those listed above and any others known to those skilled in the art.

If desired, additional layers may be included in the light-emitting device. These additional layers may include an electron injection layer (EIL), a hole blocking layer (HBL), an exciton blocking layer (EBL), and/or a hole injection layer (HIL). In addition to separate layers, some of these materials may be combined into a single layer.

In some embodiments, the light-emitting device can include an electron injection layer between the cathode layer and the light emitting layer. A number of suitable electron injection materials are known to those skilled in the art. Examples of suitable material(s) that can be included in the electron injection layer include but are not limited to, an optionally substituted compound selected from the following: aluminum quinolate ($Alq_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI) a triazine, a metal chelate of 8-hydroxyquinoline such as tris(8-hydroxyquinoliate) aluminum, and a metal thioxinoid compound such as bis(8-quinolinethiolato) zinc. In one embodiment, the electron injection layer may be aluminum quinolate ($Alq_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI), or a derivative or a combination thereof.

In some embodiments, the device can include a hole blocking layer, e.g., between the cathode and the light-emitting layer. Various suitable hole blocking materials that can be included in the hole blocking layer are known to those skilled in the art. Suitable hole blocking material(s) include but are not limited to, an optionally substituted compound selected from the following: bathocuproine (BCP), 3,4,5-triphenyl-1,2,4-triazole, 3,5-bis(4-tert-butyl-phenyl)-4-phenyl-[1,2,4] triazole, 2,9-dimethyl-4,7-diphenyl-1,10-phenanthroline, and 1,1-bis(4-bis(4-methylphenyl)aminophenyl)-cyclohexane.

In some embodiments, the light-emitting device can include an exciton blocking layer, e.g., between the light-emitting layer and the anode. In an embodiment, the band gap of the material(s) that comprise an exciton blocking layer may be large enough to substantially prevent the diffusion of excitons. A number of suitable exciton blocking materials that can be included in an exciton blocking layer are known to those skilled in the art. Examples of material(s) that can compose an exciton blocking layer include an optionally substituted compound selected from the following: aluminum quinolate ($Alq_3$), 4,4'-bis[N-(naphthyl)-N-phenyl-amino]biphenyl (NPB), 4,4'-N,N'-dicarbazole-biphenyl (CBP), and bathocuproine (BCP), and any other material(s) that have a large enough band gap to substantially prevent the diffusion of excitons.

In some embodiments, the light-emitting device can include a hole injection layer, e.g., between the light-emitting layer and the anode. Various suitable hole injection materials that can be included in the hole injection layer are known to those skilled in the art. Exemplary hole injection material(s) may include an optionally substituted compound selected from the following: a polythiophene derivative such as poly (3,4-ethylenedioxythiophene (PEDOT)/polystyrene sulphonic acid (PSS), a benzidine derivative such as N,N,N',N'-tetraphenylbenzidine, poly(N,N'-bis(4-butylphenyl)-N,N'-bis(phenyl)benzidine), a triphenylamine or phenylenediamine derivative such as N,N'-bis(4-methylphenyl)-N,N'-bis(phenyl)-1,4-phenylenediamine, 4,4',4"-tris(N-(naphthylen-2-yl)-N-phenylamino)triphenylamine, an oxadiazole derivative such as 1,3-bis(5-(4-diphenylamino) phenyl-1,3,4-oxadiazol-2-yl)benzene, a polyacetylene derivative such as poly(1,2-bis-benzylthio-acetylene), and a phthalocyanine metal complex derivative such as phthalocyanine copper. Hole-injection materials, while still being able to transport holes, may have a hole mobility substantially less than the hole mobility of conventional hole transport materials.

The emissive compositions may be prepared by adapting methods known in the art for other emissive compositions. For example, the emissive compositions may be prepared by dissolving or dispersing the electroluminescent compound (including any compound described herein) and any host (including any compound described herein), if present, in a solvent and depositing the composition on the appropriate layer of the device. The liquid may be a single phase, or may comprise one or more additional solid or liquid phases dispersed in it. The solvent may then be allowed to evaporate, or the solvent may be removed via heat or vacuum, to provide an emissive composition. Alternatively, an electroluminescent compound may be melted, or added to a molten or liquid host material (if present). The molten composition may then be applied as a layer into the device, and allowed to solidify to provide a viscous liquid or solid emissive composition layer.

Light-emitting devices comprising the compounds disclosed herein can be fabricated using techniques known in the art, as informed by the guidance provided herein. For example, a glass substrate can be coated with a high work functioning metal such as ITO which can act as an anode. After patterning the anode layer, a light-emitting layer that includes at least a compound disclosed herein, and an optional electroluminescent compound, can be deposited on the anode. The cathode layer, comprising a low work functioning metal (e.g., Mg:Ag), can then be deposited, e.g., vapor evaporated, onto the light-emitting layer. If desired, the device can also include an electron transport/injection layer, a hole blocking layer, a hole injection layer, an exciton blocking layer and/or a second light-emitting layer that can be added to the device using techniques known in the art, as informed by the guidance provided herein.

In some embodiments, the OLED may be configured by a wet process such as a process that comprises at least one of spraying, spin coating, drop casting, inkjet printing, screen printing, etc. Some embodiments provide a composition which may be a liquid suitable for deposition onto a substrate.

The liquid may be a single phase, or may comprise one or more additional solid or liquid phases dispersed in it. The liquid typically comprises a light-emitting compound, a host material disclosed herein and a solvent.

SYNTHETIC EXAMPLES

Example 1

Synthesis of Host-1

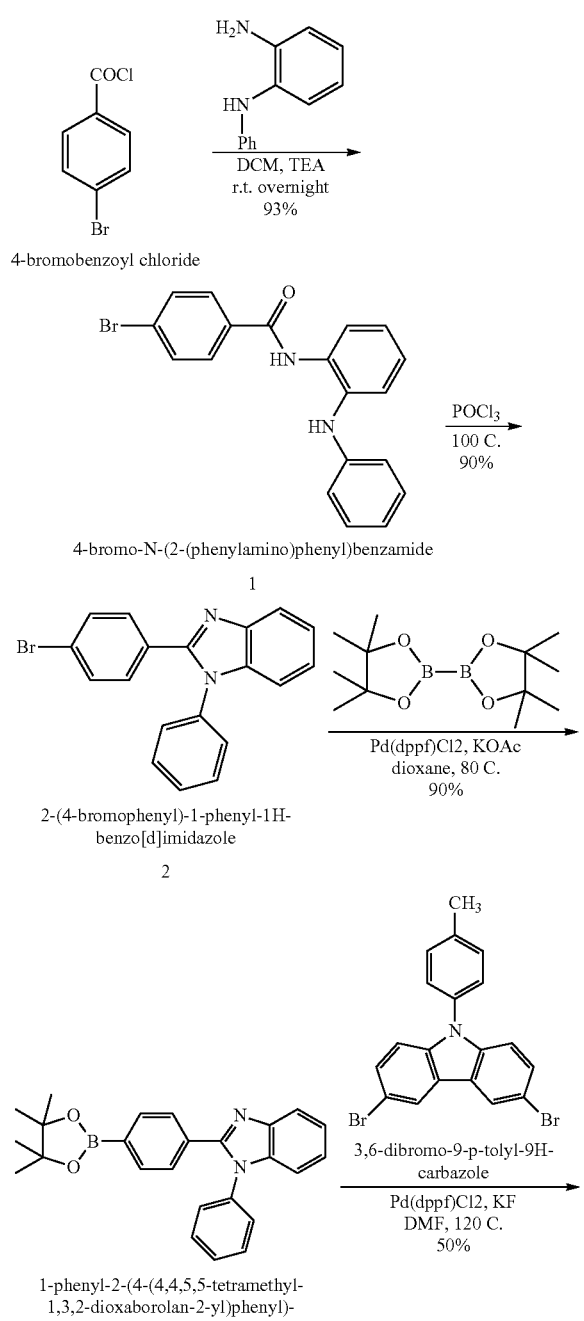

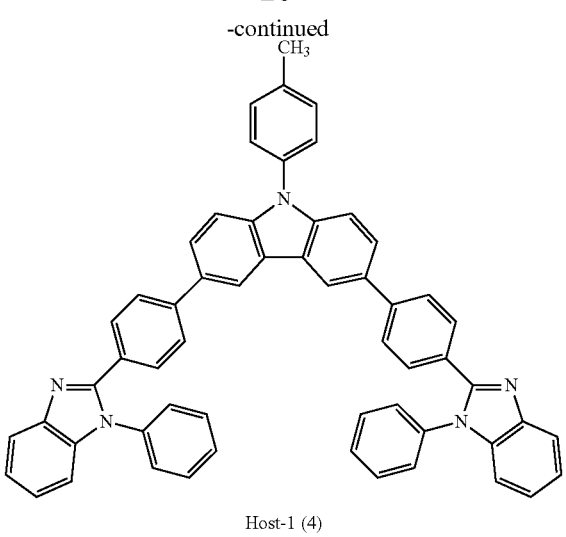

Host-1 (4)

4-Bromo-N-(2-(phenylamino)phenyl)benzamide (1): To a solution of 4-bromo-benzoyl chloride (11 g, 50 mmol) in anhydrous dichloromethane (100 ml), was added N-phenyl-benzene-1,2-diamine (10.2 g, 55 mmol), then triethylamine (17 ml, 122 mmol) slowly. The whole was stirred at room temperature overnight. Filtration gave a white solid (6.5 g). The filtrate was worked up with water (~300 ml) and extracted with dichloromethane (DCM) (~300 ml) three times. The organic phase was collected and dried over $MgSO_4$, concentrated and recrystallized in DCM/hexanes to give another portion of white solid (10.6 g). Total amount of product was 17.1 g, in 93% yield.

2-(4-bromophenyl)-1-phenyl-1H-benzo[d]imidazole (2): To a suspension of amide (1) (9.6 g, 26 mmol) in anhydrous 1,4-dioxane (100 mL) was added $POCl_3$ (9.2 mL, 100 mmol) slowly. The whole was then heated at about 100° C. overnight. After cooling to room temperature, the mixture was poured into ice (200 g) with stirring. Filtration, followed by recrystallization in DCM/hexanes gave a pale grey solid (8.2 g, in 90% yield).

1-phenyl-2-(4-(4,4,5,5-tetramethyl-1,3,2-dioxaborolan-2-yl)phenyl)-1H-benzo[d]imidazole (3): A mixture of compound (2) (0.70 g, 2 mmol), bis(pinacolate)diborane (0.533 g, 2.1 mmol), Pd(dppf)Cl$_2$ (0.060 g, 0.08 mmol) and anhydrous potassium acetate (0.393 g, 4 mmol) in 1,4-dioxane (20 mL) was heated at about 80° C. under argon overnight. After cooling to room temperature, the whole was diluted with ethyl acetate (~80 mL) then filtered. The solution was absorbed on silica gel, then purified by column chromatography (hexanes/ethyl acetate 5:1 to 3:1) to give a white solid (0.64 g, in 81% yield).

Host-1 (4): A mixture of compound (3) (2.40 g, 6.06 mmol), 3,6-dibromo-9-p-tolyl-9H-carbazole (1.245 g, 3.0 mmol), Pd(dppf)Cl$_2$ (0.23 g, 0.31 mmol) and KF (1.05 g, 18.2 mmol) in anhydrous DMF (~50 mL) was heated at about 120° C. under argon overnight. After the mixture was cooled to room temperature, it was poured into water (~200 mL) and filtered. The solid was collected and dissolved in DCM (~200 mL). After removal of water by separate funnel followed by dried over $MgSO_4$, the DCM solution was absorbed on silica gel, purified by column chromatography (hexanes/ethyl acetate 4:1 to 2:1) and precipitated from ethyl acetate/hexanes to give an off-white solid (850 mg, in 36% yield).

Example 2
Synthesis of Host-2, Host-3
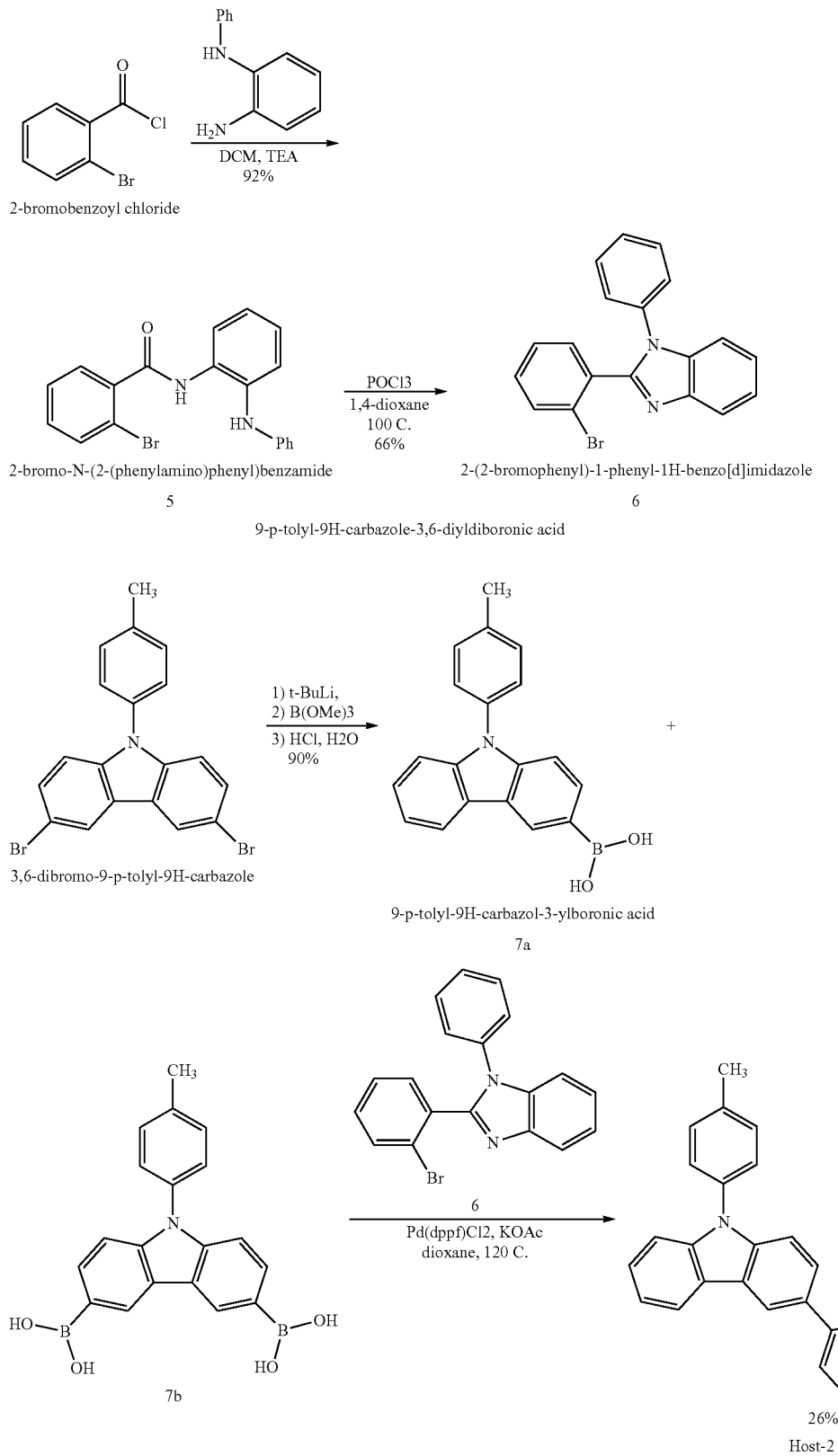

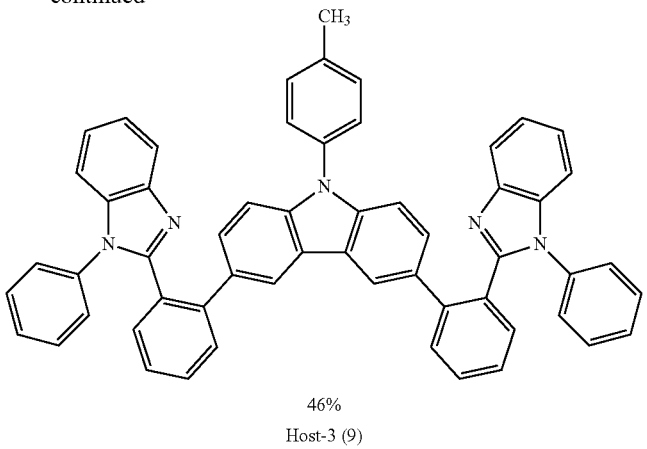

46%
Host-3 (9)

2-bromo-N-(2-(phenylamino)phenyl)benzamide (5): To a solution of N-phenylbenzene-1,2-diamine (6.08 g, 30 mmol) in anhydrous dichloromethane (~100 mL), was added 2-bromobenzoylchloride (6.585 g, 33 mmol), followed by triethylamine (7.0 mL, 50 mmol) slowly with water bath cooling. After the additions, the whole was stirred at room temperature overnight. The resulting mixture was poured into water (~150 mL) and extracted with dichloromethane (~100 mL) twice. The organic phase was collected, dried over $Na_2SO_4$, concentrated and recrystallized in dichloromethane/hexanes to give a white solid (10.7 g, in 92% yield).

2-(2-bromophenyl)-1-phenyl-1H-benzo[d]imidazole (6): To a solution of 2-bromo-N-(2-(phenylamino)phenyl)benzamide (10.7 g, 29 mmol) in anhydrous 1,4-dioxane (~100 mL), was added $POCl_3$ (6.92 g, 45 mmol) slowly. The whole was heated to about 100° C. under argon overnight. After cooling the mixture to room temperature, the mixture was poured into ice (~150 g), and then neutralized with $NaHCO_3$. After filtration, the solid was collected then dissolved in dichloromethane (~250 mL), which was washed with water (~250 mL). The aqueous solution was extracted with dichloromethane (~100 mL×2). The organic phase was combined and dried over $Na_2SO_4$, concentrated, and recrystallized in dichloromethane/hexanes to give a light grey solid (6.68 g, 66% yield).

9-p-Tolyl-9H-carbazole-3,6-diyldiboronic acid and 9-p-tolyl-9H-carbazol-3-ylboronic acid (7): To a solution of 3,6-dibromo-9-p-tolyl-9H-carbazole (4.15 g, 10 mmol) in anhydrous THF (100 mL) was added a solution of t-BuLi (1.7 M in pentane, 25 mL, 42 mmol) at about −78° C. slowly under argon. The whole was stirred for about 40 min at about −78° C., then to the resulting solution, a freshly distilled trimethyl borate (2.5 mL, 22 mmol) was added at about −78° C. After addition, the cooling bath was removed and the whole was allowed to stir at room temperature overnight.

To the resulting mixture, 5% HCl aqueous solution (~150 mL) was added and stirred overnight. The aqueous phase was separated and extracted with ethyl acetate (~150 mL×2). The organic phase was combined and dried over $Na_2SO_4$. After removal of solvent, a white solid was obtained (3.0 g), which was used for the next step without further purification. LCMS indicate the solid is a mixture of 9-p-tolyl-9H-carbazole-3,6-diyldiboronic acid and 9-p-tolyl-9H-carbazol-3-ylboronic acid (about 9:1 ratio from peak intensity).

Host-2 (8) and Host-3 (9): A mixture of 7 (1.66 g), benzimidazole 6 (1.5 g, 4.3 mmol), Pd(dppf)Cl$_2$ (200 mg, 0.27 mmol) and KF (1.4 g, 24 mmol) in DMF (40 mL) was heated at about 125° C. under argon overnight. After cooling to room temperature, the mixture was poured into water (~150 mL). The precipitate was filtered, collected, and then redissolved in dichloromethane (~100 mL). After removal of water, the dichloromethane solution was dried over $Na_2SO_4$, absorbed on silica gel, and purified by column chromatography (hexanes/ethyl acetate, gradient 5:1 to 2:1). The first blue fluorescent fraction was concentrated and recrystallized in dichloromethane/hexanes to give Host-2 (8) 600 mg, in 26% yield. The second blue fluorescent fraction was concentrated and recrystallized in dichloromethane/hexanes to give Host-3 (9) 800 mg, in 46% yield.

Example 3

Synthesis of Host-4

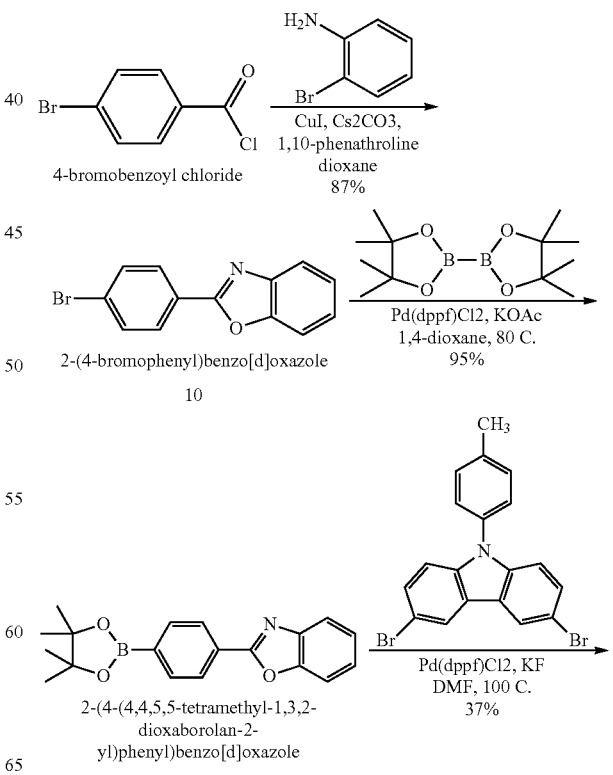

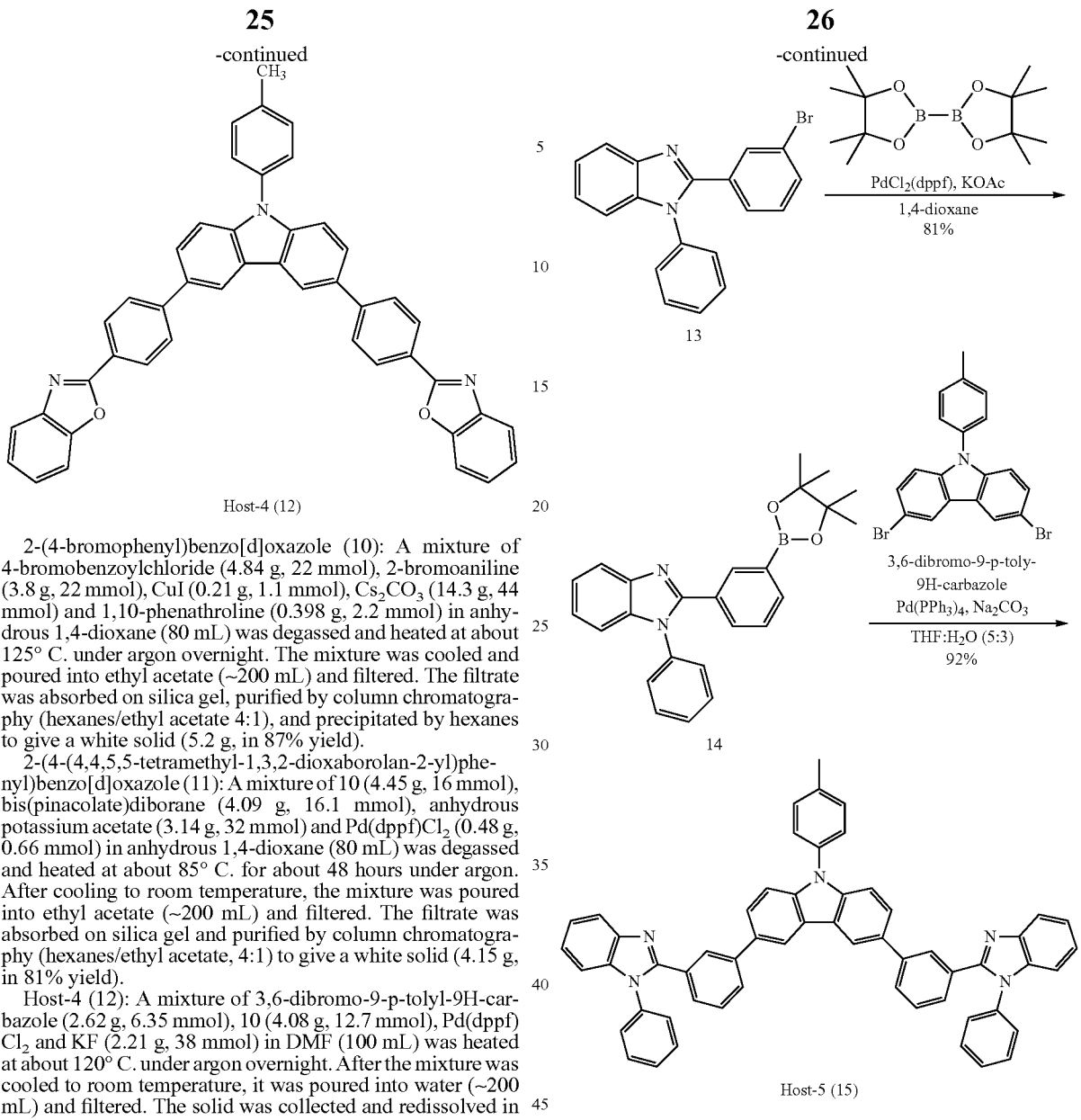

Host-4 (12)

2-(4-bromophenyl)benzo[d]oxazole (10): A mixture of 4-bromobenzoylchloride (4.84 g, 22 mmol), 2-bromoaniline (3.8 g, 22 mmol), CuI (0.21 g, 1.1 mmol), $Cs_2CO_3$ (14.3 g, 44 mmol) and 1,10-phenathroline (0.398 g, 2.2 mmol) in anhydrous 1,4-dioxane (80 mL) was degassed and heated at about 125° C. under argon overnight. The mixture was cooled and poured into ethyl acetate (~200 mL) and filtered. The filtrate was absorbed on silica gel, purified by column chromatography (hexanes/ethyl acetate 4:1), and precipitated by hexanes to give a white solid (5.2 g, in 87% yield).

2-(4-(4,4,5,5-tetramethyl-1,3,2-dioxaborolan-2-yl)phenyl)benzo[d]oxazole (11): A mixture of 10 (4.45 g, 16 mmol), bis(pinacolate)diborane (4.09 g, 16.1 mmol), anhydrous potassium acetate (3.14 g, 32 mmol) and Pd(dppf)$Cl_2$ (0.48 g, 0.66 mmol) in anhydrous 1,4-dioxane (80 mL) was degassed and heated at about 85° C. for about 48 hours under argon. After cooling to room temperature, the mixture was poured into ethyl acetate (~200 mL) and filtered. The filtrate was absorbed on silica gel and purified by column chromatography (hexanes/ethyl acetate, 4:1) to give a white solid (4.15 g, in 81% yield).

Host-4 (12): A mixture of 3,6-dibromo-9-p-tolyl-9H-carbazole (2.62 g, 6.35 mmol), 10 (4.08 g, 12.7 mmol), Pd(dppf)$Cl_2$ and KF (2.21 g, 38 mmol) in DMF (100 mL) was heated at about 120° C. under argon overnight. After the mixture was cooled to room temperature, it was poured into water (~200 mL) and filtered. The solid was collected and redissolved in chloroform (~200 mL). After the water was removed the chloroform solution was dried over $Na_2SO_4$. The chloroform solution was absorbed on silica gel, purified by column chromatography (with gradient of dichloromethane to dichloromethane/ethyl acetate 20:1), and recrystallized in dichloromethane to give a pale yellow crystalline solid (1.5 g, in 37% yield).

Example 4

Synthesis of Host-5

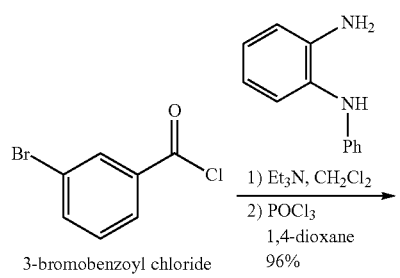

3-bromobenzoyl chloride

1) $Et_3N$, $CH_2Cl_2$
2) $POCl_3$
1,4-dioxane
96%

2-(3-bromophenyl)-1-phenyl-1H-benzo[d]imidazole (13). To a stirring solution of N-phenyl-o-phenylene-1,2-diamine (0.967 g, 5.25 mmol) in anhydrous $CH_2Cl_2$ (25 mL) was added 3-bromobenzoyl chloride (0.66 mL, 5 mmol) dropwise via syringe, followed by dropwise addition of $Et_3N$ (1.4 mL). Stirring was continued at room temperature until TLC ($SiO_2$, 4:1 hexanes-ethyl acetate) indicated consumption of the starting material (19 h). The reaction was then poured over water (~300 mL) and extracted with $CH_2Cl_2$ (3×~40 mL). The combined organics were washed with brine, dried over $MgSO_4$, filtered and concentrated. The crude intermediate was then dissolved in anhydrous 1,4-dioxane (~22 mL) and heated to about 115° C. Upon completely dissolving, phosphorus oxychloride (1.37 mL, 15 mmol) was added to the solution slowly via syringe and the reaction maintained at about 115° C. Upon completion (~2 h), the reaction was cooled to room temperature and poured over $CH_2Cl_2$ (~150 mL). The combined organics were then washed with saturated $NaHCO_3$, $H_2O$ and brine, dried over $MgSO_4$, filtered and concentrated in vacuo. The crude product was purified by flash chromatography ($SiO_2$, 4:1 hexanes-acetone) to afford 13 (1.68 g, 96%) as a light yellow solid.

1-phenyl-2-(3-(4,4,5,5-tetramethyl-1,3,2-dioxaborolan-2-yl)phenyl)-1H-benzo[d]imidazole (14). A procedure from the literature (Ge, Z.; Hayakawa, T.; Ando, S.; Ueda, M.; Akiike, T.; Miyamoto, H.; Kajita, T.; Kakimoto, M. *Chem. Mater.* 2008, 20(7), 2532-2537) was modified as follows: a mixture of 13 (4.068 g, 11.65 mmol), bis(pinacolato)diboron (6.212 g, 24.46 mmol), [1,1'-bis(diphenylphosphino)-ferrocene]dichloropalladium(II) (0.571 g, 0.699 mmol), potassium acetate (3.430, 34.94 mmol) and 1,4-dioxane (80 mL) was degassed with argon for about 1 h while stirring. The reaction mixture was then maintained at about 80° C. with stirring under argon for about 17 h. Upon completion, the reaction was cooled to room temperature, filtered through a short silica gel plug (ca. ½ in.) and the filtrant washed copiously with EtOAc (~300 mL). The combined organics were then washed with sat. NaHCO$_3$, water and brine, dried over MgSO$_4$, filtered and concentrated in vacuo. Purification of the crude product via flash chromatography (SiO$_2$, 100% CH$_2$Cl$_2$ to 49:1 CH$_2$Cl$_2$:CH$_3$OH) and subsequent recrystallization from hexanes yielded boronic ester 14 (3.72 g, 81%) as an off-white, crystalline solid.

Host-5 (15). A mixture of 14 (2.5 g, 6.309 mmol), 3,6-dibromo-9-p-tolyl-9H-carbazole (1.278 g, 3.077 mmol), tetrakis(triphenylphosphine)palladium(0) (0.178 g, 0.154 mmol), Na$_2$CO$_3$ (1.167 g, 11.01 mmol), H$_2$O (10 mL) and THF (50 mL) was degassed with argon for about 25 min while stirring. The reaction mixture was then maintained at about 85° C. with stirring under argon for about 43 h. Upon completion, the reaction was cooled to room temperature and poured over EtOAc (~150 mL). The organics were then washed with sat. NaHCO$_3$, H$_2$O and brine, dried over MgSO$_4$, filter and concentrated in vacuo. The crude product was purified via flash chromatography (SiO$_2$, 3:1 hexanes-acetone) to yield product Host-5 (15) (2.26 g, 92%) as an off-white powder.

Example 5

Synthesis of Host-6

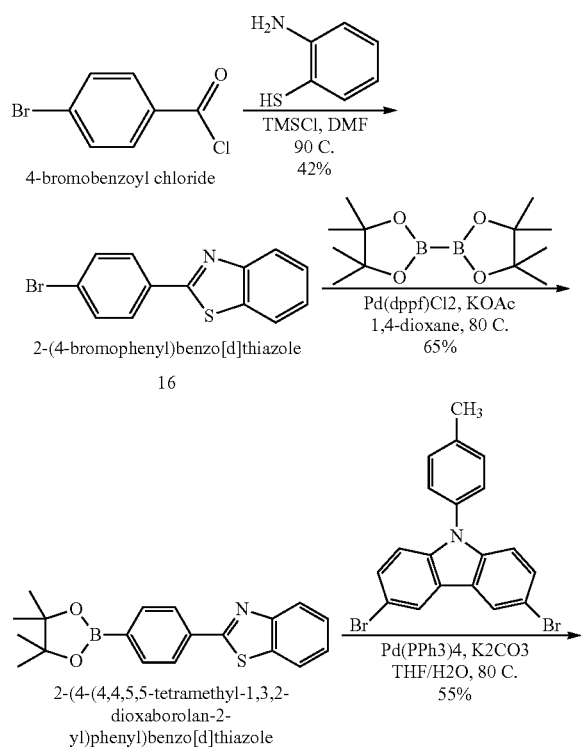

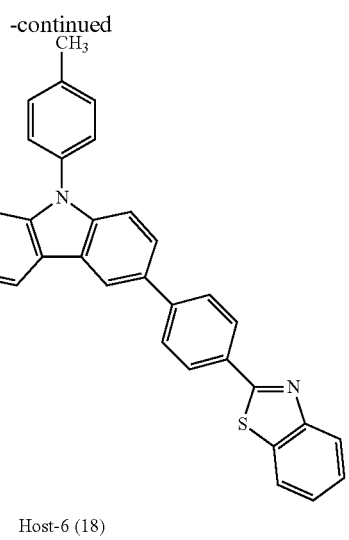

Host-6 (18)

2-(4-bromophenyl)benzo[d]thiazole (16): A mixture of 4-bromobenzoyl chloride (3.0 g, 24 mmol), 2-aminobenzenethiol (4.44 g, 24 mmol) and TMSCl (6.52 g, 60 mmol) in DMF (45 mL) was heated at about 90° C. overnight under argon. The mixture was poured into ice (300 g), and the whole was sonicated for about 20 min and yellow precipitate formed. After filtration, the solid were collected and dissolved in dichloromethane, then washed with aqueous NaHCO$_3$ (150 mL), water (150 mL) and brine (100 mL). The organic phase was dried over Na$_2$SO$_4$, loaded on silica gel, and purified by flash chromatography (hexanes/ethyl acetate 20:1). The fraction one was collected and concentrated and white solid (16) was obtained (2.89 g, 42% yield).

2-(4-(4,4,5,5-tetramethyl-1,3,2-dioxaborolan-2-yl)phenyl)benzo[d]thiazole (17): A mixture of 2-(4-bromophenyl)benzo[d]thiazole (16) (2.7 g, 9.31 mmol), bis(pinacolate)diborane (2.60 g, 10.24 mmol), Pd(dppf)Cl2 (0.341 g, 0.466 mmol) and KOAc (4.56 g, 46.6 mmol) in 1,4-dioxane (50 mL) was degassed and heated at about 80° C. overnight under argon. After cooling to room temperature, the mixture was poured into ethyl acetate (150 mL), the salts were filtered off. The solvent was removed under reduced pressure, and the resulted solid was redissolved in dichloromethane and washed with water (100 mL), brine (100 mL), and dried over Na$_2$SO$_4$. Purification with flash column chromatography (hexanes/ethyl acetate 10:1) and recrystallized in dichloromethane/hexanes gave a white solid (17) (2.04 g, 65% yield).

Host-6 compound (18): A mixture of 3,6-dibromo-9-p-tolyl-9H-carbazole (1.12 g, 2.69 mmol), 2-(4-(4,4,5,5-tetramethyl-1,3,2-dioxaborolan-2-yl)phenyl)benzo[d]thiazole (17) (2.0 g, 5.93 mmol), Pd(PPh$_3$)$_4$ (0.187 g, 0.161 mmol) and Na$_2$CO$_3$ (1.02 g, 9.6 mmol) in THF/H$_2$O (20 mL/10 mL) was degassed and heated at reflux (80° C.) overnight under argon. After cooling to room temperature, the mixture was poured into dichloromethane (100 mL). The solid was collected by filtration, then redissolved in DCM/chloroform (400 mL/400 mL), washed with water (2×400 mL) and brine (200 mL). the organic solution was dried over Na$_2$SO$_4$ and concentrated. A yellow solid (18) precipitated, which was collected by filtration (0.99 g, 55% yield).

Example 6

OLED Device Fabrication and Performance

Figure 2:
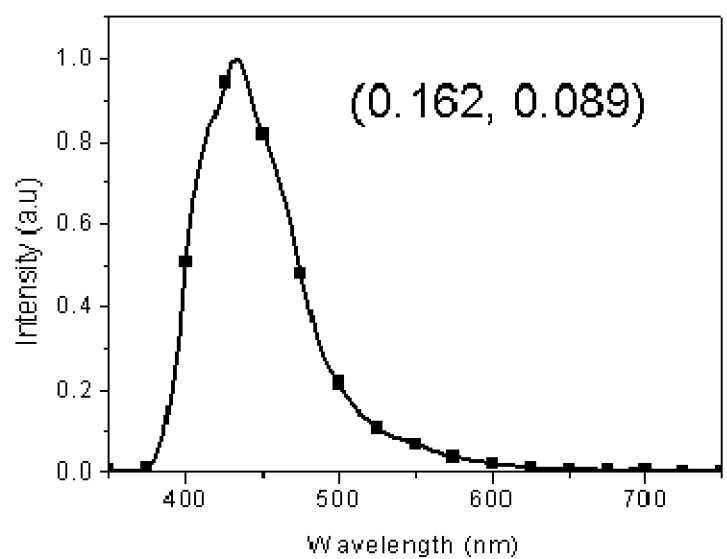
FIG. 2 is a plot depicting the electroluminescence spectrum and CIE coordinate of an embodiment of a device according to FIG. 1.
Figure 3:
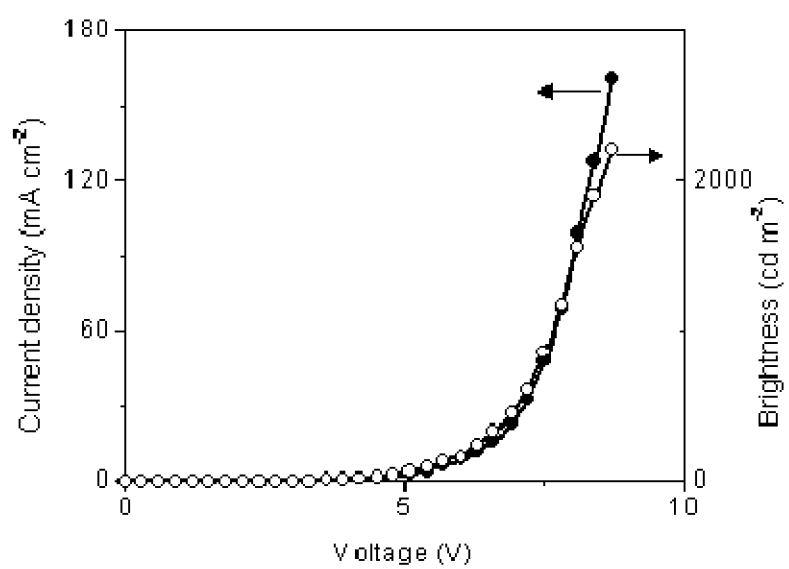
FIG. 3 is a plot depicting the current density and luminance as a function of the driving voltage of an embodiment of a device according to FIG. 1.
Figure 4:
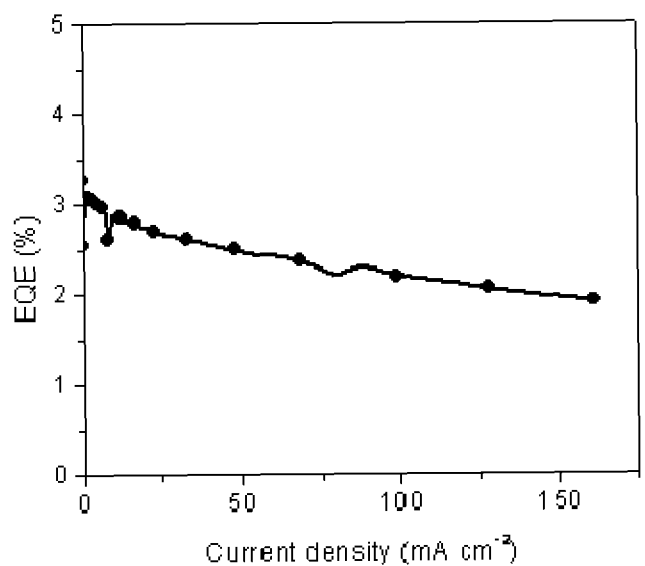
FIG. 4 is a plot depicting the external quantum efficiency and luminous efficiency as a function of current density of an embodiment of a device according to FIG. 1.
Figure 4:
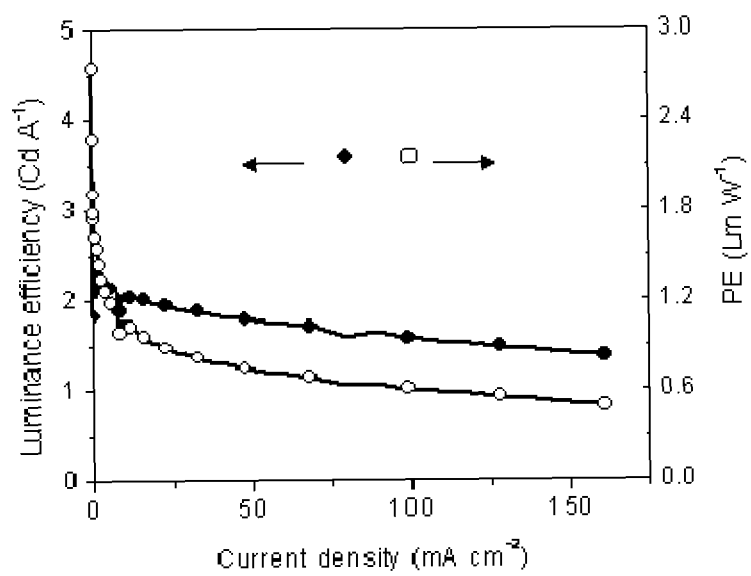

Fabrication of blue light-emitting device: the ITO coated glass substrates were cleaned by ultrasound in water, acetone, and consecutively in 2-propanol, baked at about 110° C. for about 3 hours, followed by treatment with oxygen plasma for about 5 min. A layer of PEDOT: PSS (Baytron P purchased from H.C. Starck) was spin-coated at about 3000 rpm onto the pre-cleaned and O$_2$-plasma treated (ITO)-substrate and annealed at about 180° C. for about 30 min, yielding a thickness of around 40 nm. In a glove-box hosted vacuum deposition system at a pressure of about $10^{-7}$ torr (1 torr=133.322 Pa), 4,4'4"-tri(N-carbazolyl)triphenylamine (TCTA) was first deposited on top of PEDOT/PSS layer at deposition rate of about 0.06 nm/s, yielding a 30 nm thick film. Then the Host-1 was heated and deposited on top of TCTA, yielding a 20 nm thick film, followed by deposition of 1,3,5-tris(N-phenylbenzimidizol-2-yl)benzene (TPBI) at deposition rate around 0.06 nm/s to form a 40 nm thick film. CsF (about 0.5 nm) and Al (about 150 nm) were then deposited successively at deposition rates of about 0.005 and about 0.2 nm/s, respectively. Each individual device has an area of about 0.14 cm$^2$. All spectra were measured with an Ocean Optics HR 4000 spectrometer and I-V-L characteristics were taken with a Keithley 2400 SourceMeter and Newport 2832-C power meter and 818 UV detector. All device operation was performed inside a nitrogen-filled glove-box. An exemplary configuration of the device (Device-A) is shown in FIG. 1. FIGS. 2-4 show that the device is suitable as an OLED. FIG. 2 shows electroluminescence spectrum of Device-A, plus the CIE coordinate. FIG. 3 shows current density and luminance as a function of the driving voltage of Device-A. FIG. 4 shows the luminous efficiency as a function of current density of Device-A.

Figure 5:
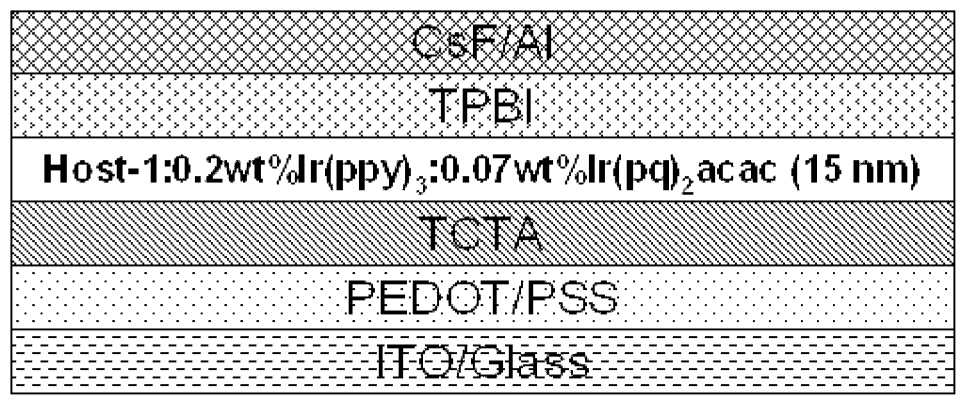
FIG. 5 is a schematic diagram of a device according to some embodiments.
Figure 6:
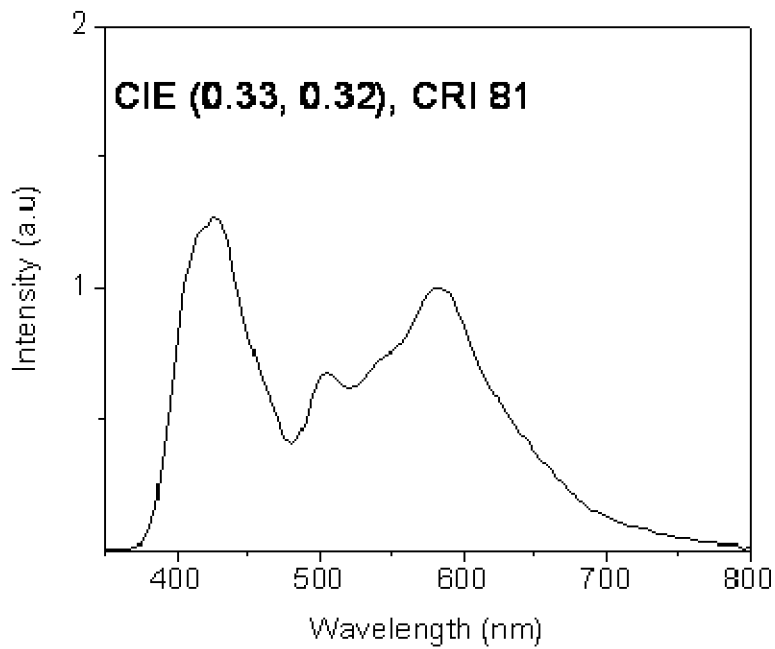
FIG. 6 is a plot depicting the electroluminescence spectrum and CIE coordinate and CRI of an embodiment of a device according to FIG. 5.
Figure 7:
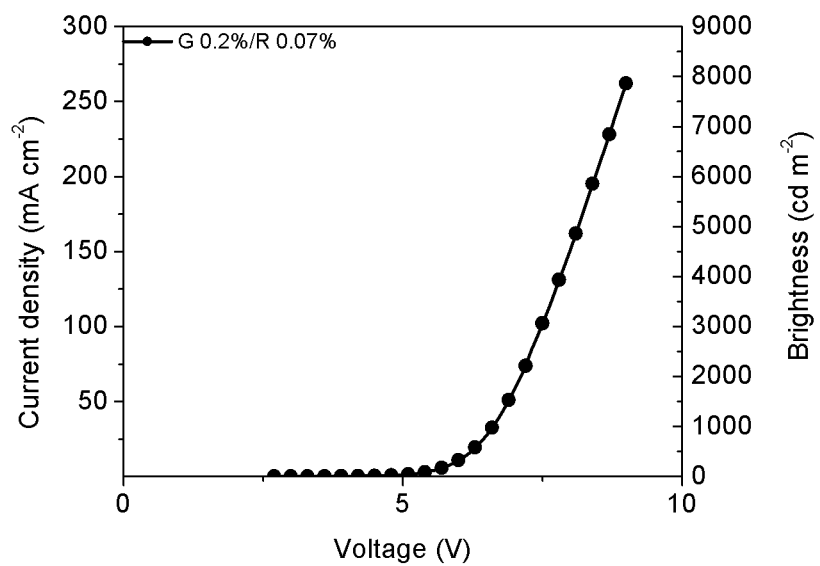
FIG. 7 is a plot depicting the current density and luminance as a function of the driving voltage of an embodiment of a device according to FIG. 5.
Figure 8:
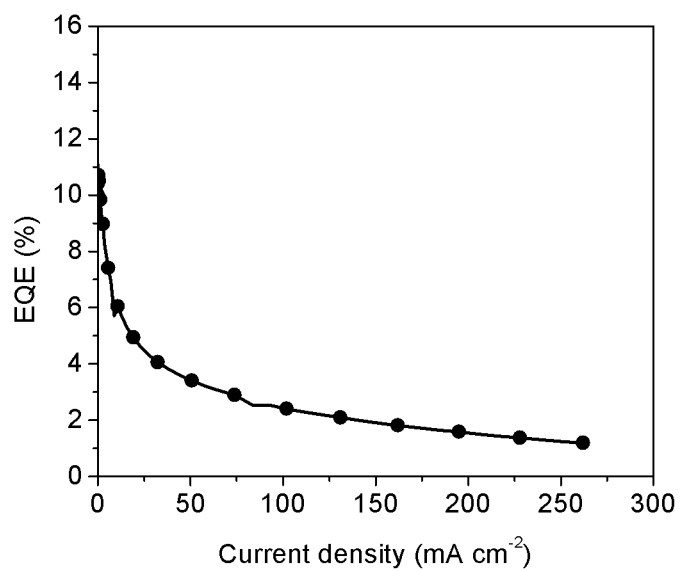
FIG. 8 is a plot depicting the external quantum efficiency as a function of current density of an embodiment of a device according to FIG. 5.

Fabrication of white light-emitting device: the ITO coated glass substrates were cleaned by ultrasound in water, acetone, and consecutively in 2-propanol, baked at 110° C. for about 3 hours, followed by treatment with oxygen plasma for about 5 min. A layer of PEDOT: PSS (Baytron P purchased from H.C. Starck) was spin-coated at about 3000 rpm onto the pre-cleaned and O2-plasma treated (ITO)-substrate and annealed at about 180° C. for about 30 min, yielding a thickness of around 40 nm. In a glove-box hosted vacuum deposition system at a pressure of about $10^{-7}$ torr (1 torr=133.322 Pa), 4,4'4"-tri(N-carbazolyl)triphenylamine (TCTA) was first deposited on top of PEDOT/PSS layer at deposition rate of about 0.06 nm/s, yielding a 30 nm thick film. Then the Host-1 and green emitter and red emitter Ir(pq)$_2$acac were concurrently heated and deposited on top of TCTA under a different deposition speed to make Ir(ppy)$_3$ at about 0.2 wt % and Ir(pq)$_2$acac at about 0.07 wt %, yielding a 15 nm thick emissive layer, followed by deposition of 1,3,5-tris(N-phenylbenzimidizol-2-yl)benzene (TPBI) at deposition rate around 0.06 nm/s to form a 40 nm thick film. CsF (0.5 nm) and Al (150 nm) were then deposited successively at deposition rates of about 0.005 and about 0.2 nm/s, respectively. Each individual device has an area of about 0.14 cm$^2$. All spectra were measured with an Ocean Optics HR 4000 spectrometer and I-V-L characteristics were taken with a Keithley 2400 SourceMeter and Newport 2832-C power meter and 818 UV detector. All device operation was performed inside a nitrogen-filled glove-box. An exemplary configuration of the device (Device-B) is shown in FIG. 5. FIGS. 6-8 show that the device is suitable as an OLED. FIG. 6 shows electroluminescence spectrum of Device-B, plus the CIE coordinate. FIG. 7 shows current density and luminance as a function of the driving voltage of Device-B. FIG. 8 shows the external quantum efficiency as a function of current density of Device-B.

Although the claims have been described in the context of some specific embodiments and examples, it will be understood by those skilled in the art that the scope of the claims extend beyond the specifically disclosed embodiments to other alternative embodiments and/or uses of the invention and obvious modifications and equivalents thereof.

What is claimed is:
1. A compound selected from the groups consisting of:

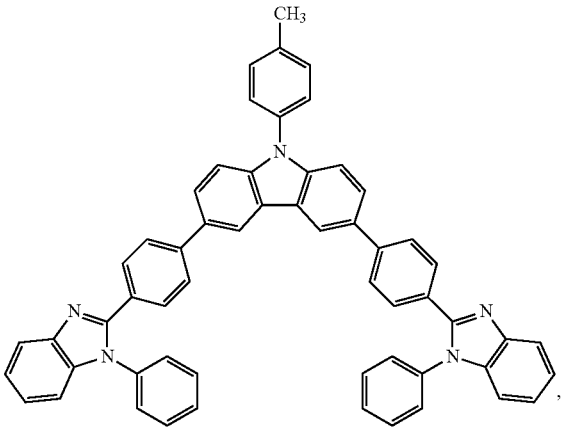

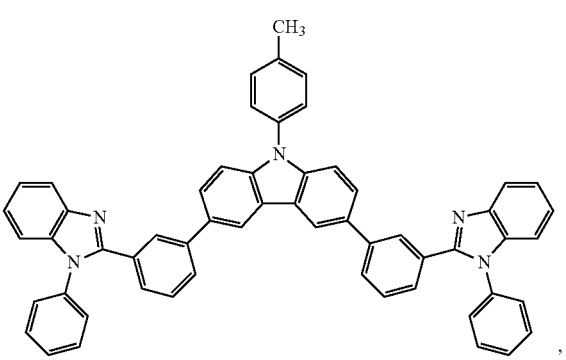

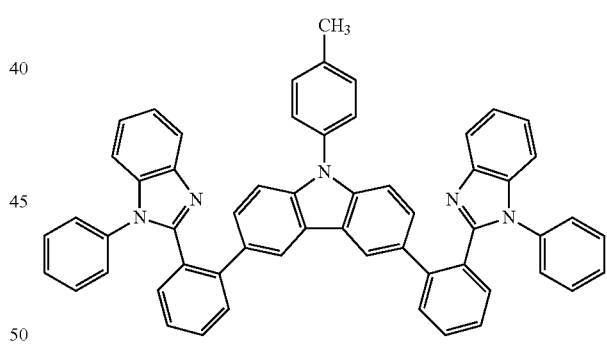

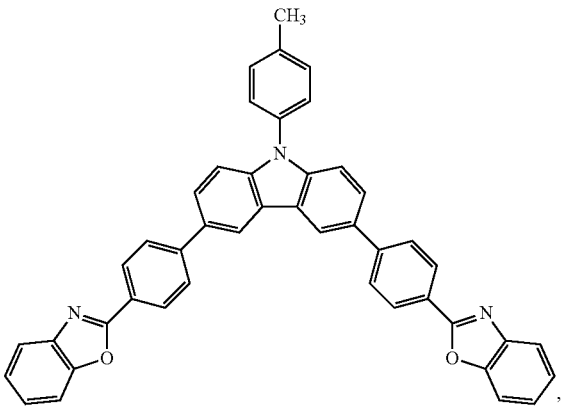

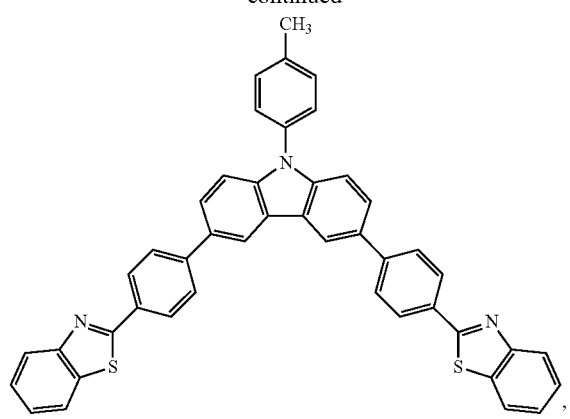
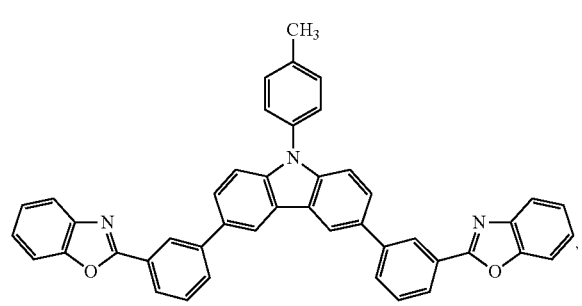
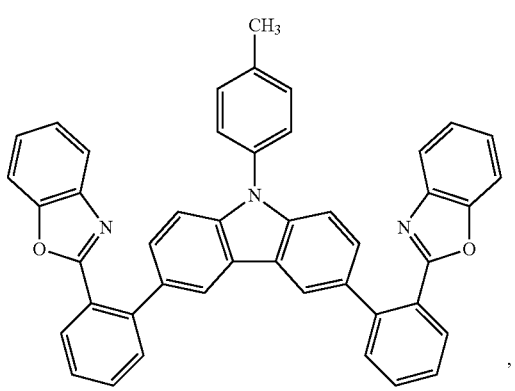
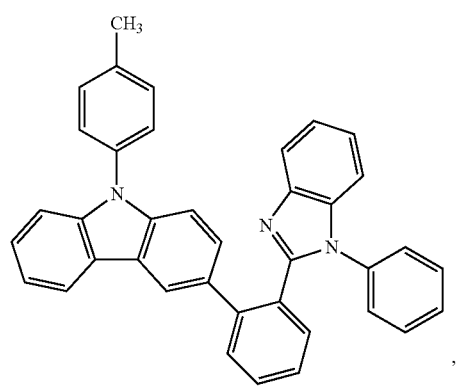
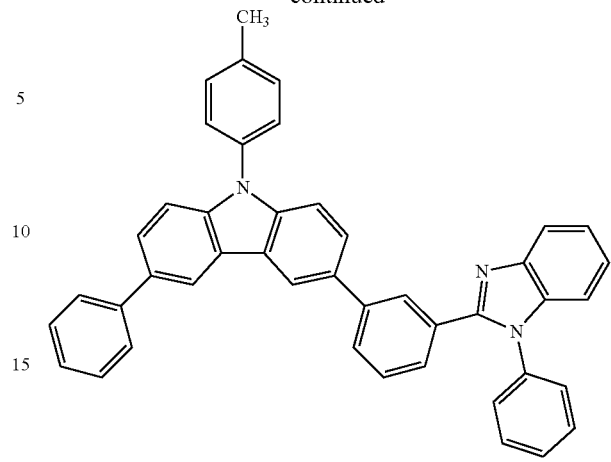
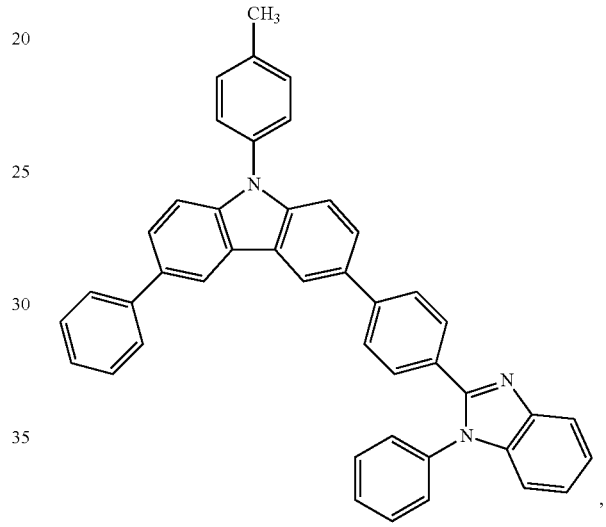
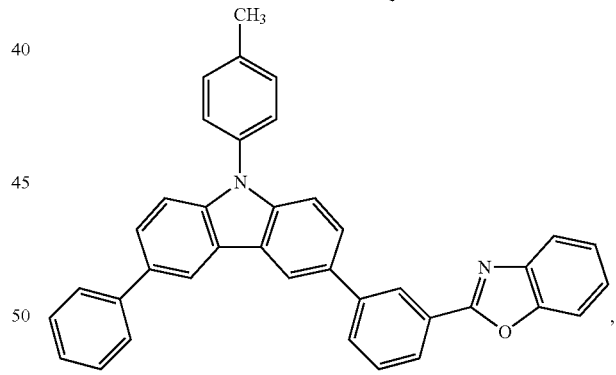
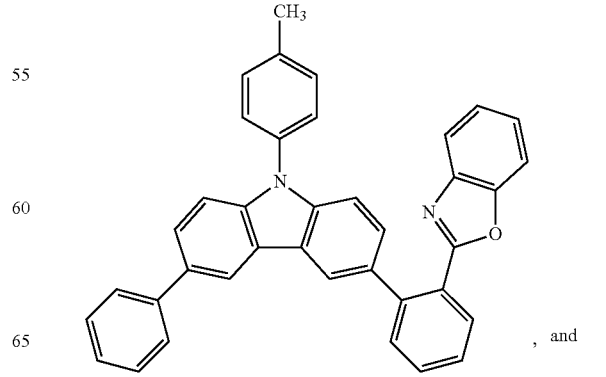
, and -continued
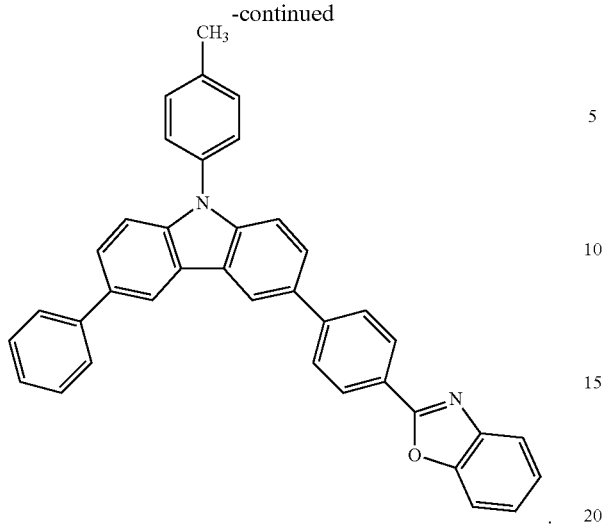
2. An organic light emitting diode (OLED) device comprising:
   a light emitting layer comprising an electroluminescent compound and a host;
   wherein the host comprises a compound according to claim 1.
* * * * *